United States Patent
Jain et al.

(10) Patent No.: US 12,133,854 B2
(45) Date of Patent: *Nov. 5, 2024

(54) PHARMACEUTICAL COMPOSITIONS OF MIFEPRISTONE

(71) Applicant: SLAYBACK PHARMA LLC, Princeton, NJ (US)

(72) Inventors: Paras P. Jain, Maharashtra (IN); Somnath Devidas Navgire, Telangana (IN); Sumitra Ashokkumar Pillai, Telangana (IN)

(73) Assignee: SLAYBACK PHARMA LLC, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/530,815

(22) Filed: Dec. 6, 2023

(65) Prior Publication Data

US 2024/0122944 A1   Apr. 18, 2024

Related U.S. Application Data

(63) Continuation of application No. 17/843,669, filed on Jun. 17, 2022, now Pat. No. 11,878,025.

(30) Foreign Application Priority Data

Sep. 6, 2021 (IN) .............................. 202141040290

(51) Int. Cl.
| | |
|---|---|
| *A61K 31/567* | (2006.01) |
| *A61K 9/127* | (2006.01) |
| *A61K 9/14* | (2006.01) |
| *A61K 9/16* | (2006.01) |
| *A61K 9/20* | (2006.01) |
| *A61K 9/50* | (2006.01) |

(52) U.S. Cl.
CPC .......... *A61K 31/567* (2013.01); *A61K 9/1272* (2013.01); *A61K 9/141* (2013.01); *A61K 9/1629* (2013.01); *A61K 9/5021* (2013.01)

(58) Field of Classification Search
None
See application file for complete search history.

(56) References Cited

U.S. PATENT DOCUMENTS

| | | | |
|---|---|---|---|
| 6,362,173 B1 | 3/2002 | Schatzberg et al. | |
| 11,878,025 B2 * | 1/2024 | Jain ..................... | A61K 9/1272 |
| 2005/0170004 A1 | 8/2005 | Rosenberger et al. | |
| 2007/0106828 A1 | 6/2007 | Joshi et al. | |
| 2009/0004262 A1 | 1/2009 | Shaw et al. | |
| 2010/0278921 A1 | 11/2010 | Fischer et al. | |
| 2010/0297194 A1 | 11/2010 | Catron et al. | |
| 2015/0258118 A1 | 9/2015 | Battung et al. | |
| 2016/0213684 A1 | 7/2016 | Battung et al. | |
| 2016/0220505 A1 | 8/2016 | Temtsin Krayz et al. | |

FOREIGN PATENT DOCUMENTS

| | | |
|---|---|---|
| CN | 101455671 A | 6/2009 |
| EA | 1 990 044 A1 | 11/2008 |
| WO | WO 2008/083192 A2 | 7/2008 |
| WO | WO 2010/082149 A1 | 7/2010 |
| WO | WO 2013/036195 A2 | 3/2013 |
| WO | WO 2019/152808 A1 | 8/2019 |

OTHER PUBLICATIONS

He et al., "Improved bioavailability of orally administered mifepristone from PLGA nanoparticles," International Journal of Pharmaceutics, 2007, vol. 334, pp. 173-178.
Hou et al., "The production and characteristics of solid lipid nanoparticles (SLNs)," Biomaterials, 2003, vol. 24, pp. 1781-1785.
International Search Report and Written Opinion of the International Searching Authority for International Application No. PCT/US22/34024, dated Sep. 19, 2022.
Verma et al., "Formulation, Design and Development of Mifepristone Immediate Release Tablet," Intl. Journal of Pharma Sciences and Research, 2014, pp. 760-769.
Wu et al., "Physical and chemical stability of drug nanoparticles," Advanced Drug Delivery Review, 2011. vol. 63, pp. 456-469.
Zhang et al., "Chitosan-based nanoparticle for improved anticancer efficacy and bioavailability of mifepristone," Beilstein J. Nanotechnol, 2016, vol. 7, pp. 1861-1870.

* cited by examiner

*Primary Examiner* — Lakshmi S Channavajjala
(74) *Attorney, Agent, or Firm* — Birch, Stewart, Kolasch & Birch, LLP

(57) ABSTRACT

Pharmaceutical compositions and stable nano-suspensions comprising mifepristone and at least one pharmaceutically acceptable excipient, which exhibit enhanced bioavailability compared to the currently marketed or commercially available formulations. Manufacturing process and methods of use are also provided. The pharmaceutical compositions are used for prevention, treatment or prophylaxis of disorders in human patients in need thereof. Oral pharmaceutical compositions of mifepristone, methods for their administration, processes for their production, and use of these compositions are described for the treatment of diseases for which mifepristone is indicated.

12 Claims, No Drawings

PHARMACEUTICAL COMPOSITIONS OF MIFEPRISTONE

CROSS-REFERENCE TO RELATED APPLICATIONS

This application is a Continuation of co-pending application Ser. No. 17/843,669, filed Jun. 17, 2022, which claims foreign priority to Indian Application No. IN 202141040290, filed on Sep. 6, 2021, which is incorporated herein by reference in its entirety.

FIELD OF THE INVENTION

The present invention relates to pharmaceutical compositions comprising mifepristone, which is a glucocorticoid antagonist, and at least one pharmaceutically acceptable excipient, wherein the inventive pharmaceutical compositions exhibit enhanced bioavailability compared to a reference drug product, such as the currently marketed or commercially available formulations. The present invention further provides manufacturing process and use of the inventive compositions for the prevention, treatment or prophylaxis of disorders in human patients in need thereof.

In particular, the present invention relates to oral pharmaceutical compositions and stable nano-suspensions of mifepristone particles, methods for their administration, processes for their production, and use of these compositions for treatment of diseases treatable by mifepristone.

BACKGROUND OF THE INVENTION

Mifepristone is a potent antagonist of steroid hormone receptors such as glucocorticoid, progesterone and androgen receptors. Mifepristone is a selective antagonist of the progesterone receptor at low doses and blocks the glucocorticoid receptor at higher doses. Mifepristone is used for termination of pregnancy and to treat disorders like Cushing's syndrome and different types of proliferative disorders. The chemical name of mifepristone is 11β-(4-dimethylaminophenyl)-17β-hydroxy-17α-(1-propynyl)-estra-4,9-dien-3-one. The structural formula is:

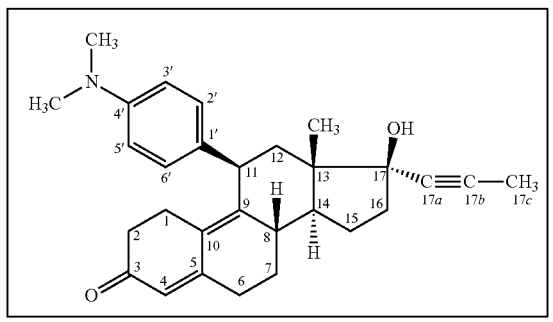

Mifepristone is currently marketed under the brand name KORLYM® (300 mg; National Drug Code Number 76346-073; NDA 202107).

KORLYM® is available in the form of film-coated tablets containing 300 mg of mifepristone. KORLYM® film-coated tablets (300 mg; National Drug Code Number 76346-073; NDA 202107) contain inactive ingredients such as silicified microcrystalline cellulose, sodium starch glycolate, hydroxypropyl cellulose, sodium lauryl sulfate, magnesium stearate, hypromellose, titanium dioxide, triacetin, D&C yellow 10 aluminum lake, polysorbate 80, and FD&C yellow 6 aluminum lake. KORLYM® is used to treat high blood sugar (hyperglycemia) caused by high cortisol levels in the blood (hypercortisolism) in adults with endogenous Cushing's syndrome who have type 2 diabetes mellitus or glucose intolerance and have failed surgery or cannot have surgery.

Cushing's syndrome of endogenous origin is a hormonal disease associated with an increased blood concentration of cortisol (hypercortisolism) or the presence in blood of glucocorticoid hormone excess over a long period of time. Cushing's syndrome is classified as either ACTH dependent or non-ACTH dependent.

Adrenocorticotropic hormone (ACTH) dependent Cushing's syndrome is characterized by a chronic ACTH hypersecretion which stimulates the growth of the adrenal glands and the hypersecretion of corticosteroids. The most common underlying cause of ACTH dependent Cushing's syndrome is excessive production of ACTH by pituitary adenomas. Cushing's syndrome resulting from the production of ACTH in another location than the pituitary gland is known as ectopic Cushing's syndrome. Examples of ectopic sites include thymoma, medullary carcinoma of the thyroid, pheochromocytoma, islet cell tumors of the pancreas and small cell carcinoma of the lung.

The package insert of KORLYM® discloses that the patients are instructed to take the tablet once daily with a meal. The daily dose of KORLYM® may be increased in 300 mg increments. The dose of KORLYM® may be increased to a maximum of 1200 mg once daily but should not exceed 20 mg/kg per day. Increases in dose should not occur more frequently than once every 2-4 weeks. Decisions about dose increases should be based on a clinical assessment of tolerability and degree of improvement in Cushing's syndrome manifestations. Changes in glucose control, antidiabetic medication requirements, insulin levels, and psychiatric symptoms may provide an early assessment of response (within 6 weeks) and may help guide early dose titration.

Following oral administration, time to peak plasma concentrations of mifepristone occurs between 1 and 2 hours following single dose, and between 1 and 4 hours following multiple doses of 600 mg of KORLYM® in healthy volunteers.

Mean plasma concentrations of three active metabolites of mifepristone peak between 2 and 8 hours after multiple doses of 600 mg/day, and the combined concentrations of the metabolites exceed that of the parent mifepristone. Exposure to mifepristone is substantially less than dose proportional. Time to steady state is within 2 weeks, and the mean (SD) half-life of the parent mifepristone was 85 (61) hours following multiple doses of 600 mg/day of KORLYM®.

Mifepristone is primarily metabolized by N-demethylation and terminal hydroxylation of the 17-propynyl chain of mifepristone. In-vitro studies have shown that CYP450 3A4 is primarily responsible for metabolism. The three major metabolites identified in humans are: (1) RU42633, the most widely found in plasma, is the N-mono-demethylated metabolite; (2) RU42848, which results from the loss of two methyl groups from the 4-dimethylaminophenyl in position 11β; and (3) RU42698, which results from terminal hydroxylation of the 17-propynyl chain.

Peak mean plasma concentrations of three active metabolites of mifepristone were attained between 2 and 8 hours after multiple doses of 600 mg/day, and the combined concentrations of the metabolites exceed that of the parent mifepristone. Time to attain steady state is within 2 weeks, and the mean half-life of the parent mifepristone was 85 hours following multiple doses of 600 mg/day of KORLYM®. KORLYM® demonstrates a significant increase in plasma levels of mifepristone when dosed with food.

The drug absorption after oral administration generally depends on (i) the release of the drug from the composition, (ii) the dissolution of the drug under physiological conditions and (iii) its permeability across the gastrointestinal tract. A higher dissolution rate of a composition generally increases release of the drug from its composition, which is a prerequisite for adequate bioavailability of a drug. Because of this requirement, a good in vitro dissolution of the composition may lead to good and adequate in vivo plasma concentration and therefore an adequate bioavailability.

Mifepristone is very soluble in methanol, chloroform and acetone and practically insoluble in water. Mifepristone demonstrates a pH-related solubility profile. Solubility of mifepristone is dramatically high in acid (~25 mg/mL at pH 1.5) and declines rapidly as pH increases (i.e., above pH 2.5 the solubility of mifepristone is less than 1 mg/mL). Mifepristone is poorly water soluble and hence, it would be difficult to formulate and deliver oral dosage forms which exhibit good bioavailability.

Mifepristone is characterized as a Biopharmaceutical Classification System (BCS) class IV compound, which means that it has low aqueous solubility and low permeability. For BCS class IV drugs like mifepristone, the dissolution step is the rate-determining factor in drug absorption. Current strategies employed to improve the apparent solubility of a drug include the use of: (i) co-solvents (e.g., low molecular weight polyethylene glycols and propylene glycol) in combination with water to dissolve the drug; (ii) complexing agents (e.g., cyclodextrins and its derivatives) to form water-soluble inclusion complexes of the drug or (iii) hydrophilic excipients (e.g., polyvinylpyrrolidones and high molecular weight polyethylene glycols) as drug carriers for the preparation of solid dispersions in which the drug is dispersed molecularly or as ultrafine crystals. However, drug precipitation is a common problem faced by these formulations. The drugs tend to precipitate in vivo due to a sudden pH change from stomach to intestine, formulation dilution by body fluids, or digestion of solubilizing excipients in formulations. Such precipitation usually leads to a low oral bioavailability with a delayed response or reduced efficacy. As a result, in vivo drug precipitation poses a great challenge for the development of oral formulations and dosage form development.

The need for administering such high doses of mifepristone may be due to the low bioavailability exhibited by KORLYM® and may be responsible for the adverse side effects associated with the use of mifepristone such as nausea or emesis, dizziness and diarrhea. Moreover, low bioavailability results in more variable absorption and potential variability of the desired therapeutic response.

Thus, there exists a need to develop pharmaceutical compositions of mifepristone, which increase the bioavailability of mifepristone, thereby reducing the dose of mifepristone which must be administered to a human subject for a therapeutic effect, and resulting in reduced adverse events and enhanced patient safety.

SUMMARY OF THE INVENTION

The present invention addresses this need by providing pharmaceutical compositions comprising mifepristone and at least one pharmaceutically acceptable excipient, wherein the inventive pharmaceutical compositions exhibit enhanced bioavailability compared to the currently marketed or commercially available formulations. Due to the increased bioavailability or absorption, the dosage according to the invention can be lower than the usual or the conventional dose typically required to produce equal or higher therapeutic effect, and may also reduce the side effects and limit the risk to the patient.

The present invention also provides compositions to improve the bioavailability of mifepristone in the fed state and provide a composition which maintains optimal therapeutic concentrations of mifepristone in the human subject, and at the same time reduces the side effects exhibited by the same.

In certain embodiments, the compositions for oral administration according to the present invention provide mifepristone to a patient population with lower variability in bioavailability, thus providing consistent pharmacokinetic parameters (e.g., a narrower observed range for $C_{max}$ and AUC values) across patient population to whom the composition is administered.

The pharmaceutical compositions of mifepristone according to the invention, upon oral administration, provide enhanced bioavailability of mifepristone in the fed or fasted state compared to a reference drug product. As used herein, the reference drug product, is a currently marketed or commercially available formulation. In certain embodiments, the KORLYM® drug product (National Drug Code Number 76346-073; NDA 202107), available as a 300 mg tablet, is the reference composition. The increase in oral bioavailability may enable administration of mifepristone at a significantly lower therapeutically effective doses than what are currently being used.

The compositions of mifepristone according to the invention are suitable for oral administration to patients, and can provide uniform plasma level(s) and sufficient mifepristone exposure (AUC) in fasted and fed state when compared to commercially available formulation (e.g., KORLYM®). Also, the inventive oral compositions of mifepristone, when administered to a human subject, exhibit less variability in pharmacokinetic parameters (e.g., $C_{max}$, $AUC_{0-t}$ and/or $AUC_{0-infinity}$) than a commercially available reference mifepristone formulation of the same dosage (e.g., KORLYM®).

The composition of mifepristone according to the invention provide stable pharmaceutical compositions of mifepristone suitable for oral administration, exhibiting improved solubility and increased bioavailability of mifepristone when compared to the commercially available reference drug product (such as KORLYM®), wherein the composition remains stable for at least 6 months at 40° C.s/75% RH ("relative humidity") or 25° C./60% RH ("relative humidity").

The inventive compositions for oral administration provide enhanced bioavailability of mifepristone in the fed and/or fasted states compared to commercially available reference formulation, e.g., KORLYM®. In an aspect, the present invention relates to inventive composition comprising mifepristone suitable for oral administration, wherein said composition exhibits enhanced bioavailability in the fed state, compared to commercially available product (KORLYM®).

In an aspect, the dose of inventive pharmaceutical composition comprising mifepristone is reduced by at least 10% in comparison to commercially available product (KORLYM®). In one aspect, the pharmaceutical compositions may exhibit at least about 15% enhanced bioavailability in the fed state, compared to a drug product corresponding to a reference composition having the same dosage.

In another aspect, the dose of inventive pharmaceutical composition comprising mifepristone is reduced by at least 20% in comparison to commercially available product (KORLYM®). In another aspect, the dose of inventive pharmaceutical composition comprising mifepristone is reduced by at least 30% in comparison to commercially available product (KORLYM®). In another aspect, the dose of inventive pharmaceutical composition comprising mifepristone, is reduced by at least 50% in comparison to commercially available product (KORLYM®). In another aspect, the dose of inventive pharmaceutical composition comprising mifepristone, is reduced by at least 75% in comparison to commercially available product (KORLYM®).

In an aspect, the inventive pharmaceutical composition comprising mifepristone exhibits less variability in pharmacokinetic parameters ($C_{max}$, $AUC_{0-t}$ and/or $AUC_{0-infinity}$) compared to a commercially available reference product (such as KORLYM®), when administered orally to human subjects.

In an aspect, the present invention relates to nano-suspension compositions of mifepristone. The present invention further relates to stable pharmaceutical composition for oral administration comprising the nano-suspension compositions of mifepristone.

In an aspect, the invention relates to a pharmaceutical composition comprising a therapeutically effective amount of mifepristone particles and at least one pharmaceutically acceptable excipient, wherein the mifepristone particles have an average D90 particle size equal to or less than about 1000 nm. In another aspect, the invention relates to stable nano-suspensions comprising: (a) a therapeutically effective amount of nano-sized mifepristone particles; and (b) at least one suspension-aid, wherein the nano-sized mifepristone particles have an average D90 particle size equal to or less than about 1000 nm. Preferably, the stable nano-suspensions further comprising at least one surfactant. For instance, the stable nano-suspensions may comprise or consist of: (a) nano-sized mifepristone; (b) a suspension-aid comprising hydroxypropyl methylcellulose; and (c) a surfactant comprising sodium lauryl sulphate and (d) surface stabilizer comprising docusate sodium.

The pharmaceutical compositions and the stable nano-suspensions, may have at least one pharmaceutically acceptable excipient that comprises: (a) at least one suspension-aid; (b) at least one surfactant; and (c) optionally, one or more other pharmaceutically acceptable excipients. Preferably, the at least one suspension-aid is selected from the group consisting of hydroxypropyl methyl cellulose acetate succinate (HPMC-AS), polyvinyl pyrrolidine and vinyl acetate (PVP/VA) copolymer, hydroxypropyl methylcellulose phthalate (HPMCP), hydroxypropyl methylcellulose (HPMC), polyethylene glycol (PEG), hydroxypropyl cellulose (HPC), carboxymethyl cellulose (CMC), polyvinyl pyrrolidine (PVP), and mixtures thereof. Preferably, the at least one surfactant is sodium lauryl sulphate.

In other aspect, the present invention also relates to methods for making nano-suspension of mifepristone, methods for preparing pharmaceutical composition, and methods for treating disorders using the inventive pharmaceutical composition.

In an aspect, the inventive pharmaceutical composition suitable for oral administration to a human subject in need thereof, comprises nano-suspension of mifepristone; wherein said composition exhibits enhanced bioavailability in the fed state compared to commercially available reference product (such as KORLYM®).

In an aspect, the inventive pharmaceutical composition suitable for oral administration to a human subject in need thereof, comprises nano-suspension of mifepristone; wherein said composition exhibits enhanced bioavailability in the fasted state compared to commercially available product (such as KORLYM®).

In another aspect, the pharmaceutical composition suitable for oral administration to a human subject in need thereof, comprises a nano-sized mifepristone, wherein the composition remains stable for at least 6 months at 40° C./75% RH ("relative humidity") or 25° C./60% RH ("relative humidity").

Each of the aspects described in this application may further have one or more of the following additional elements in any combination:
- Element 1: the nano-suspension of mifepristone may comprise a pharmaceutically acceptable suspension-aid.
- Element 2: the nano-suspension of mifepristone may comprise at least one pharmaceutically acceptable suspension-aid, at least one surfactant and/or at least one surface stabilizer.
- Element 3: the nano-suspension of mifepristone may comprise at least one suspension-aid, at least one surfactant, at least one surface stabilizer and optionally one or more pharmaceutically acceptable excipient.
- Element 4: the nano-suspension of mifepristone may be prepared by wet media milling process.
- Element 5: the nano-particles have a mean diameter selected from the group consisting of a mean diameter of less than about 1000 nm, preferably less than 800 nm.
- Element 6: the nano-suspension of mifepristone may have a weight ratio of the mifepristone to the pharmaceutically acceptable suspension-aid from about 1:1 to about 20:1. The amount of the at least one surface stabilizer is preferably from about 0.05% w/w to about 1% w/w of a total weight of the pharmaceutical composition, e.g., an amount of the at least one surface stabilizer may be from about 0.05% w/w to about 1% w/w of a total core table weight.
- Element 7: the nano-suspension of mifepristone may comprise at least one suspension-aid selected from hydroxypropyl methyl cellulose acetate succinate (HPMC-AS), polyvinyl pyrrolidine and vinyl acetate (PVP/VA) copolymer, hydroxypropyl methylcellulose phthalate (HPMCP), hydroxypropyl methylcellulose (HPMC), polyethylene glycol (PEG), hydroxypropyl cellulose (HPC), carboxymethyl cellulose (CMC), polyvinyl pyrrolidine (PVP), and mixtures thereof.
- Element 8: the nano-suspension of mifepristone may comprise at least one surfactant (for example, but not limited to sodium lauryl sulphate).
- Element 9: the nano-suspension of mifepristone may further comprise one or more pharmaceutically acceptable excipients selected from the group consisting of diluents, binders, disintegrants, lubricants, glidants, surfactants, solubilizers, plasticizers, surface stabilizers, antioxidants and combinations thereof.
- Element 10: the inventive pharmaceutical compositions may comprise from about 100 mg to about 1200 mg of mifepristone, preferably about 240 mg.
- Element 11: the inventive pharmaceutical compositions may preferably be in the form of a tablet, a capsule, a caplet, beads, granules, powder or oral suspension.

Element 12: the inventive pharmaceutical compositions may further comprise one or more pharmaceutically acceptable excipients selected from the group consisting of diluents, binders, disintegrants, lubricants, glidants, surfactants, plasticizers, solubilizers, surface stabilizers, antioxidants and combinations thereof.

Element 13: the inventive pharmaceutical compositions may preferably be obtained by direct compression, wet granulation or dry granulation.

Element 14: the inventive pharmaceutical compositions may preferably be in the form of a tablet or capsule comprising: (a) nano-sized mifepristone (b) at least one intra-granular material, (c) at least one extra-granular material, and (d) optionally, coating. In certain aspects, in the pharmaceutical compositions (a) the at least one intra-granular material is selected from the group consisting of silicified microcrystalline cellulose, sodium starch glycolate, and mixtures thereof, and (b) the least one extra-granular material is selected from the group consisting of microcrystalline cellulose, sodium starch glycolate, colloidal silicon dioxide, magnesium stearate, and mixtures thereof.

Element 15: the inventive pharmaceutical compositions may preferably be in the form of a tablet comprising: the nano-suspension of mifepristone can be sprayed over or mixed with at least one intra-granular material.

Element 16: the inventive pharmaceutical compositions may preferably be in the form of a tablet comprising: the nano-suspension of mifepristone can be sprayed over or mixed with at least one intra-granular material, wherein intra-granular material contains one or more of the following excipients selected from the group consisting of diluents, binders, disintegrants, lubricants, glidants, surfactants, plasticizers, solubilizers, surface stabilizers, antioxidants and combinations thereof.

Element 17: the inventive pharmaceutical composition preferably has the level of total related substances that is less than about 5% (w/w), preferably less than about 4% (w/w), preferably less than about 3% (w/w), preferably less than about 2% (w/w), preferably less than about 1% (w/w) preferably less than about 1.5% (w/w) and more preferably less than about 0.5 (w/w) as measured by HPLC, when stored at 25° C./60% RH for at least 3 months.

Element 18: the inventive pharmaceutical composition preferably has a level of any unknown impurity that is less than about 1% (w/w), preferably less than about 0.5% (w/w), preferably less than about 0.25% (w/w), preferably less than about 0.15% (w/w) and more preferably less than about 0.1% (w/w) as measured by HPLC, when stored at 25° C./60% RH for at least 3 months.

Element 19: the inventive pharmaceutical compositions for oral administration exhibits faster dissolution rate of mifepristone compared to commercially available reference formulation (such as KORLYM®).

Element 20: the inventive pharmaceutical compositions for oral administration provides enhanced bioavailability of mifepristone in fasting or fed state compared to commercially available reference formulation (such as KORLYM®).

Element 21: the inventive pharmaceutical compositions for oral administration provides enhanced bioavailability of mifepristone in fasting and fed states which in turn reduces the dose of mifepristone which can be administered to a human subject compared to commercially available reference formulation (such as KORLYM®).

Element 22: the inventive mifepristone compositions may preferably be used in a method for treating proliferative disorder in a human subject, which method comprises: (a) providing a pharmaceutical composition; and (b) providing instructions for oral administration of the composition indicating that the composition can be administered to a human subject with food.

Element 23: in the inventive pharmaceutical compositions, at least 50% of the mifepristone is released after about 30 minutes as determined using USP Apparatus II at 50 RPM in pH 1.8 KCl buffer 900 mL dissolution media at 37° C.

Element 24: in the inventive pharmaceutical compositions, at least 70% of the mifepristone is released after about 45 minutes as determined using USP Apparatus II at 50 RPM in pH 1.8 KCl buffer 900 mL dissolution media at 37° C.

Element 25: in the inventive pharmaceutical compositions, at least 50% of the mifepristone is released after about 30 minutes as determined using USP Apparatus II at 75 RPM in 0.01 N HCL 900 mL dissolution media at 37° C.

Element 26: the nano-suspension of mifepristone may have a weight ratio of the mifepristone to the pharmaceutically acceptable suspension-aid from about 20:1 to about 1:20.

Element 27: the nano-suspension of mifepristone may have a weight ratio of the mifepristone to surfactant from about 50:1 to about 1:50. The amount of the at least one surface stabilizer is preferably from about 0.05% w/w to about 1% w/w of a total weight of the pharmaceutical composition, e.g., an amount of the at least one surface stabilizer may be from about 0.05% w/w to about 1% w/w of a total core table weight.

Element 28: a pharmaceutical composition comprising an effective amount of the stable nano-suspension according to the invention, together with a pharmaceutically acceptable carrier, excipient or diluent.

Element 29: a method of treatment for Cushing's syndrome, or the use of a pharmaceutical composition as defined herein for the manufacture of a medicament for the treatment of Cushing's syndrome. In an aspect, the inventive pharmaceutical compositions are used in a method of treatment or for the manufacture of a medicament for the treatment of high blood sugar (hyperglycemia) caused by high cortisol levels in the blood (hypercortisolism) in adults with endogenous Cushing's syndrome who have type 2 diabetes mellitus or glucose intolerance and have failed surgery or cannot have surgery.

By way of non-limiting examples, exemplary combinations applicable to the embodiments described in this application may include any combination with one or more of the elements described above.

By way of non-limiting example, exemplary combinations applicable to the embodiments described in this application may include any combination with one or more of the elements described above.

DETAILED DESCRIPTION OF THE INVENTION

Unless defined otherwise, all the technical and scientific terms used herein have the same meanings as commonly known by a person skilled in the art. In case of conflict, the definitions provided herein will prevail. Unless specified otherwise, all the percentages, portions and ratios in the present invention are on weight basis.

Unless otherwise indicated, all numbers expressing quantities of ingredients, properties such as molecular weight, reaction conditions, and so forth used in the present specification and associated claims are to be understood as being modified in all instances by the term "about." The terms "about" and "approximate," when used along with a numerical variable, generally means the value of the variable and all the values of the variable within a measurement or an experimental error (e.g., 95% confidence interval for the mean) or within a specified value (e.g., ±20%, ±10%, ±5%) within a broader range. For instance, the term "about" typically means having a value falling within an accepted standard of error of the mean when considered by one of ordinary skill in the art. Preferably, the term "about" refers to ±20%, preferably ±10%, and more preferably ±5% of the value or range to which it refers.

Accordingly, unless indicated to the contrary, the numerical parameters set forth in the following specification and attached claims are approximations that may vary depending upon the desired properties sought to be obtained by the embodiments of the present invention. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces.

While compositions and methods are described herein in terms of "comprising" various components or steps, the compositions and methods can also "consist essentially of" or "consist of" the various components and steps.

As used herein the term "mifepristone" refers to mifepristone free base or its pharmaceutically acceptable salts, solvates or hydrates thereof. In principle, any crystalline form or amorphous form of mifepristone may be used for manufacturing the inventive pharmaceutical compositions of the present invention.

The term "pharmaceutically acceptable" substances mean those, which, according to a common medical judgment, are suitable to be in contact with a tissue of a patient without any inappropriate toxicity, irritation, allergic response, etc., have a reasonable balance between advantages and disadvantages, and can be applied to its target use effectively.

The term "pharmaceutically acceptable salt" refers to mifepristone salts which are formed with inorganic or organic acids.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The term "particles" refers to individual drug substance particles whether the particles exist singly or are agglomerated. Thus, a composition comprising particulate mifepristone may contain agglomerates that are well beyond the size limit of about 1 μm specified herein. However, if the mean size of the primary drug substance particles (i.e., mifepristone) comprising the agglomerate are less than about 1 μm individually, then the agglomerate itself is considered to satisfy the particle size constraints defined herein and the composition is within the scope of the invention.

The terms "nano-particle(s)" and "nano-sized" refers to mifepristone particles produced by the methods of this invention that in general have an average (arithmetic mean) diameter of <1 μm, particularly between about 1-1000 nm, about 10-800 nm, about 50-700 nm, about 100-700 nm. The average diameter of a nano-particle may be determined as the "average effective particle diameter", which may be measured by e.g., dynamic light scattering methods, or microscopy.

The term "particle-size distribution" (PSD), as used herein, refers to the relative amounts of particles present, sorted according to size.

The terms "pharmaceutical composition," "pharmaceutical product," "pharmaceutical dosage form," "dosage form," "composition", "formulation", etc., refer to a pharmaceutical composition administered to a patient in need of treatment, including but not limited to tablet, hard-gelatin capsule, soft-gelatin capsule, oral suspension, oral solution, enteric coated hard-gelatin capsule, enteric coated soft-gelatin capsule, to cores, coated cores, pellets, micro pellets, pills, compressed tablets, granules, spheres, capsules and the like.

By "effective amount" or "therapeutically effective amount" is meant the amount of a drug sufficient to treat, prevent, or ameliorate a condition in a subject or patient. The effective amount of mifepristone or pharmaceutically acceptable salt thereof, used to practice the present invention for therapeutic management of a condition may be determined and adjusted by a person of ordinary skill to provide the appropriate amount and dosage regimen, e.g., depending upon one or more of the manner of administration, the age, body weight, sex, and/or general health of the patient.

The term "solubility" means solubility of mifepristone or its pharmaceutically acceptable salts in media such as water, buffer, gastrointestinal simulated fluid, gastrointestinal fluid and the like.

The term "in vivo" in general means in the living body of a plant or animal, whereas the term "in vitro" generally means outside the body and in an artificial environment.

The term "reduced dose" as used herein refers to a therapeutically effective dose of mifepristone, which is less than the usual or conventional dose required to produce equal or higher therapeutic effect.

The term "subject" refers to an animal, including a human or non-human. The terms patient and subject may be used interchangeably herein.

The term "bioavailability" indicates the extent to which a drug or another substance is utilized by a target tissue after administration. For example, "bioavailability" may refer to the fraction of drug absorbed following administration to a subject or patient under fed or fasted state.

The term "bioequivalence" refers to the absence of a significant difference between the bioavailability, e.g., the mean ratio of AUC (over 24 hours) and the mean ratio of $C_{max}$ is within 80% to 125% between two pharmaceutical drug products (e.g., a test composition and a reference composition) over the course of a period of time, at the same dose and under the same conditions. The determination of whether or not a test composition is bioequivalent to a reference composition is determined by performing a study, referred to as a bioequivalence or comparative bioavailability study, in a group of subjects under controlled conditions.

The term "peak time of plasma drug concentration ($T_{max}$)" means the time when peak plasma drug concentration ($C_{max}$) is attained after drug administration.

The term "peak plasma drug concentration ($C_{max}$)" means the maximum plasma drug concentration attained after drug administration.

The term "$AUC_{0\text{-}infinity}$" means the area under a plasma drug concentration-time curve from time point of 0 to infinity after drug administration.

The term "$AUC_{0\text{-}t}$" means the area under a plasma drug concentration-time curve from time point of 0 to t after drug administration, "1" is time in hours may range from 24-72 hour.

As used herein, the term "enhanced bioavailability" refers to increase in concentration of the active ingredient in the body fluid provided by the compositions of the present invention when compared to concentration of the active ingredient in the body fluid obtained from KORLYM® under identical conditions. In certain aspects, the bioavailability (e.g., AUC, $C_{max}$ and/or $T_{max}$) of mifepristone when formulated as described herein is enhanced at least about 15%, but may be greater than 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, 300%, 325%, 350%, 375% or 400% of the dose administered when compared to KORLYM® under identical conditions.

Pharmacokinetic parameters for the inventive pharmaceutical compositions can be measured in a single or multiple dose study using a replicate or a non-replicate design. For example, but not limited to, the pharmacokinetic parameters can be measured in a single dose pharmacokinetic study using a two-period, two-sequence crossover design. Alternately, a four-period, replicate design crossover study may also be used. Pharmacokinetic parameters characterizing rate and extent of mifepristone absorption are evaluated statistically. The area under the plasma concentration-time curve from time zero to the time of measurement of the last quantifiable concentration ($AUC_{0\text{-}t}$) and to infinity ($AUC_{0\text{-}infinity}$), $C_{max}$, and $T_{max}$ can be determined according to standard techniques. Statistical analysis of pharmacokinetic data is performed on logarithmic transformed data (e.g., $AUC_{0\text{-}t}$, $AUC_{0\text{-}infinity}$, or $C_{max}$ data) using analysis of variance (ANOVA).

Reference throughout this specification will be made to the administration of a pharmaceutical composition under fed conditions or fasted conditions. It is well understood in the art that the pharmacokinetic performance of some compositions is affected by the presence or absence of food in the gastro-intestinal system. These references thus relate to the normally accepted administration circumstances that are referred to in the art as "fed" or "fasted."

The term "food effect" as used herein means food-drug interactions which either decrease or increase the extent of drug absorption. In other words, the bioavailability for a drug is altered when administered under fasted state, in comparison to the drug when administered in the fed state. It may refer to a relative difference in one or more of $AUC_{0\text{-}infinity}$, $AUC_{0\text{-}t}$ and/or $C_{max}$ of a drug, when said drug or a formulation thereof is administered orally to a human, concomitantly with food or in a fed state as compared to the same values when the same formulation is administered in a fasted state or without food.

In certain aspects, the food effect may be defined as the ratio of the $C_{max}$ and/or AUC values of the tested drug in fed versus fasted states. Measuring the $C_{max}$ and/or AUC values of the tested drug in fed and in fasted states is standard practice in the art. Reduction of food effect can be determined by comparing the value of the ratio from the composition or pharmaceutical composition of the invention and the value of a composition without the solubilized form disclosed in the present invention.

In certain aspects, the pharmaceutical compositions described herein reduce or eliminate the food effect. As used herein, "reducing the food effect" refers to narrowing the difference in bioavailability, e.g., $AUC_{0\text{-}infinity}$, $AUC_{0\text{-}t}$ and/or $C_{max}$ for a drug administered under fasted states in comparison to the drug administered under fed states. In certain aspects, the food effect is eliminated. Thus, upon oral administration of a pharmaceutical composition as described herein, to a mammal in need thereof, there is not a significant food effect. In other words, the difference between a pharmacokinetic parameter measured after oral administration to a mammal with and without food, respectively, is less than 40%, e.g., less than 35%, less than 30%, less than 25%, less than 20%, less than 15%, less than 10 or less than 5%. Preferably the composition or the pharmaceutical composition of the invention has at least 15% reduced food effect, preferably 20%, preferably 25%, preferably 30%, preferably 40%, reduced food effect.

In an embodiment, the inventive pharmaceutical composition as described herein, wherein said composition upon oral administration in fed state exhibits bioequivalence to a commercially available reference drug product corresponding to National Drug Code Number 76346-073 and NDA 202107 (KORLYM®), in the fed state, and wherein said bioequivalence is established by at least one of: (i) a confidence interval for mean $AUC_{0\text{-}t}$ between about 80% and about 125%; (ii) a confidence interval for mean $AUC_{0\text{-}infinity}$ between about 80% and about 125%; (iii) a confidence interval for mean $C_{max}$ between about 80% and about 125% or combinations thereof.

In an embodiment, the inventive pharmaceutical composition comprising: (a) 240 mg mifepristone; and (b) one or more pharmaceutically acceptable excipients; wherein said composition upon oral administration, in fed state, exhibits bioequivalence to reference drug product corresponding to National Drug Code Number 76346-073 and NDA 202107 (KORLYM®), in the fed state, and wherein said bioequivalence is established by at least one of: (i) a confidence interval for least square geometric mean of $AUC_{0\text{-}t}$ between about 80% and about 125%; (ii) a confidence interval for least square geometric mean of $AUC_{0\text{-}infinity}$ between about 80% and about 125%; (iii) a confidence interval for least square geometric mean of $C_{max}$ between about 80% and about 125% or combinations thereof.

The difference in AUC of the compositions of the present invention, when administered in the fed versus the fasted state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

The difference in $C_{max}$ of the compositions of the present invention, when administered in fed versus the fasted state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

In some aspects, administration of the pharmaceutical composition to fed and fasted subjects produce a coefficient of variation in $AUC_{0-t}$, $C_{max}$ and/or $AUC_{0-infinity}$ of less than about 60% (e.g., less than 55%, 50%, 45%, 40%, 35%, 30%, 25%, 20%, and 15%). In particular embodiments, the coefficient of variation in $AUC_{0-t}$, $C_{max}$ and/or $AUC_{0-infinity}$ is of from about 20% to about 60% (e.g., from 20% to 30%, from 20% to 35%, from 20% to 40%, from 20% to 45%, from 20% to 50%, from 20% to 55%, from 30% to 35%, from 30% to 40%, from 30% to 45%, from 30% to 50%, from 30% to 55%, from 30% to 60%, from 35% to 40%, from 35% to 45%, from 35% to 50%, from 35% to 55%, from 35% to 60%, from 40% to 45%, from 40% to 50%, from 40% to 55%, from 40% to 60%, from 45% to 50%, from 45% to 55%, from 45% to 60%, from 50% to 55%, from 50% to 60%, and from 55% to 60%).

The difference in $AUC_{0-t}$ of the compositions of the present invention, when administered in fasting versus fed state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

The difference in $AUC_{0-t}$ of the compositions of the present invention, when administered in fed versus fed state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

The difference in $C_{max}$ of the compositions of the present invention, when administered in fasting versus the fed state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%

The difference in $C_{max}$ of the compositions of the present invention, when administered in fed versus the fed state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

In some aspects, administration of the pharmaceutical composition to fasting and fed subjects produce a coefficient of variation in $AUC_{0-t}$, $C_{max}$ and/or $AUC_{0-infinity}$ of less than about 60% (e.g., less than 55%, 50%, 45%, 40%, 35%, 30%, 25%, 20%, and 15%). In particular embodiments, the coefficient of variation in $C_{max}$ and/or $AUC0-t$ is of from about 20% to about 60% (e.g., from 20% to 30%, from 20% to 35%, from 20% to 40%, from 20% to 45%, from 20% to 50%, from 20% to 55%, from 30% to 35%, from 30% to 40%, from 30% to 45%, from 30% to 50%, from 30% to 55%, from 30% to 60%, from 35% to 40%, from 35% to 45%, from 35% to 50%, from 35% to 55%, from 35% to 60%, from 40% to 45%, from 40% to 50%, from 40% to 55%, from 40% to 60%, from 45% to 50%, from 45% to 55%, from 45% to 60%, from 50% to 55%, from 50% to 60%, and from 55% to 60%).

The nano-particles of a solid material, and in particular nano-particles of a poorly soluble or essentially insoluble solid material, finds beneficial use in numerous applications related to the increase in surface area achieved as a result of size reduction. When incorporated into a mixture, formula, composition, dispersion, coating, powder, lyophilizate, suspension, matrix, and the like, a solid material in the form of smaller particles exhibit greater homogeneity in macroscopic and improved microscopic or kinetic properties such as increased rate of dissolution into a volume of solvent or a volume of liquid including a pseudo-infinite solvent pool volume.

The nano-particles of a solid material often requires presence of one or more surface-active substance particularly on the surface of the particles to achieve or augment particle stability.

In certain embodiments, following oral administration of the inventive pharmaceutical compositions enhances the bioavailability of the mifepristone relative to the reference composition, making it possible to use reduced doses of mifepristone (e.g., 100, 110, 120, 130, 140, 150, 160, 170, 180, 190, 200, 210, 220, 230, 240, 250, 260 and 270 mg) while achieving same or substantially similar therapeutic efficacy as compared to the commercially approved dose (300 mg). On the other hand, the inventive pharmaceutical composition allows administration of a lower dose while retaining the therapeutic efficacy of mifepristone (e.g., 100, 110, 120, 130, 140, 150, 160, 170, 180, 190, 200, 210, 220, 230, 240, 250, 260 and 270 mg), resulting in reduced undesirable side effects such as nausea, fatigue, headache, decreased blood potassium, arthralgia, vomiting, peripheral edema, hypertension, dizziness, decreased appetite, endometrial hypertrophy, associated with the use of conventional dose.

In certain embodiments, following oral administration of the inventive pharmaceutical compositions enhances the bioavailability of the mifepristone making it possible to use reduced doses of mifepristone (e.g., 480 mg) while achieving same or substantially similar therapeutic efficacy as compared to the commercially approved dose of KORLYM® (i.e., 600 mg). On the other hand, the inventive pharmaceutical composition allows administration of a lower dose while retaining the therapeutic efficacy of mifepristone (e.g., 480 mg), resulting in reduced undesirable side effects such as nausea, fatigue, headache, decreased blood potassium, arthralgia, vomiting, peripheral edema, hypertension, dizziness, decreased appetite, endometrial hypertrophy, associated with the use of conventional dose of KORLYM® (i.e., 600 mg).

In certain embodiments, following oral administration of the inventive pharmaceutical compositions enhances the bioavailability of the mifepristone making it possible to use reduced doses of mifepristone (e.g., 720 mg) while achieving same or substantially similar therapeutic efficacy as compared to the commercially approved dose of KORLYM® (i.e., 900 mg). On the other hand, the inventive pharmaceutical composition allows administration of a lower dose while retaining the therapeutic efficacy of mifepristone (e.g., 720 mg), resulting in reduced undesirable side effects such as nausea, fatigue, headache, decreased blood potassium, arthralgia, vomiting, peripheral edema, hypertension, dizziness, decreased appetite, endometrial hypertrophy, associated with the use of conventional dose of KORLYM® (i.e., 900 mg).

In certain embodiments, following oral administration of the inventive pharmaceutical compositions enhances the bioavailability of the mifepristone making it possible to use reduced doses of mifepristone (e.g., 960 mg) while achieving same or substantially similar therapeutic efficacy as compared to the commercially approved dose of KORLYM® (i.e., 1200 mg). On the other hand, the inventive pharmaceutical composition allows administration of a lower dose while retaining the therapeutic efficacy of mifepristone (e.g., 960 mg), resulting in reduced undesirable side effects such as nausea, fatigue, headache, decreased blood potassium, arthralgia, vomiting, peripheral edema, hypertension, dizziness, decreased appetite, endometrial hypertrophy, associated with the use of conventional dose of KORLYM® (i.e., 1200 mg).

In certain embodiments, following oral administration of the inventive pharmaceutical composition to subjects (e.g., in fed or fasted condition), the mean bioavailability is greater than about 20% (e.g., greater than 25%, 30%, 35%, 40%, 45%, 50%, 55%, 60%, 65%, 70%, 75%, 80%, 85%, 90%, 95%, or even 99%) or between about 20% to about 90% (e.g., from 20% to 30%, from 20% to 40%, from 20% to 50%, from 20% to 60%, from 20% to 70%, from 20% to 80%, from 20% to 90%, from 30% to 40%, from 30% to 50%, from 30% to 60%, from 30% to 70%, from 30% to 80%, from 30% to 90%, from 40% to 50%, from 40% to 60%, from 40% to 70%, from 40% to 80%, from 40% to 90%, from 50% to 60%, from 50% to 70%, from 50% to 80%, from 50% to 90%, from 60% to 70%, from 60% to 80%, from 60% to 90%, from 70% to 80%, from 70% to 90%, and from 80% to 90%).

In an embodiment, composition comprising effective amount of nano-particles of mifepristone, exhibits a level of total related substances less than about 5% (w/w), preferably less than about 4% (w/w), preferably less than about 3% (w/w), preferably less than about 2% (w/w), preferably less than about 1.5% (w/w), preferably less than about 1% (w/w), preferably less than about 0.5 (w/w) as measured by HPLC.

In an embodiment, composition comprising an effective amount of nano-particles of mifepristone, exhibits a level of any unknown impurity less than about 1% (w/w), preferably less than about 0.5% (w/w), preferably less than about 0.4% (w/w), preferably less than about 0.3% (w/w), preferably less than about 0.2% (w/w), preferably less than about 0.15% (w/w), more preferably less than about 0.1% (w/w) as measured by HPLC.

Certain embodiments herein relate to inventive pharmaceutical compositions which are stable, e.g., stable over the shelf life of the drug product. As used herein, the term "stable" is defined as no more than about 5% loss of mifepristone under typical commercial storage conditions. In certain embodiments, the compositions of the present invention will have no more than about 3% loss of mifepristone, more preferably, no more than about 2% loss of mifepristone, under typical commercial storage conditions. The composition retains at least about 95% of the potency of mifepristone after storing the composition at 40° C. and 75% relative humidity for at least three months. In certain aspects, the term "stable" refers to chemical stability, wherein preferably not more than 2% w/w of total related substances, more preferably not more than 1.5% w/w of total related substances are formed on storage at accelerated conditions of stability at 40° C. and 75% relative humidity or at 25° C. and 60% relative humidity for a period of at least three months or to the extent necessary for use of the composition. In certain aspects, the term "stable" refers to that the mifepristone particles do not appreciably flocculate or agglomerate due to interparticle attractive forces, or otherwise significantly increase in particle size over time.

An embodiment relates to a pharmaceutical composition comprising an effective amount of mifepristone, wherein the level of any unknown impurity is less than about 1% (w/w), preferably less than about 0.8% (w/w), preferably less than about 0.5% (w/w) as measured by HPLC, when stored at 25° C./60% RH for at least 3 months.

In particular, the N-Desmethyl mifepristone impurity (i.e., (11β-[4-(Methylamino) phenyl]-17β-hydroxy-17α-(1-propynyl) estra-4,9-dien-3-one) may be monitored. The structure of N-Desmethyl mifepristone is shown below:

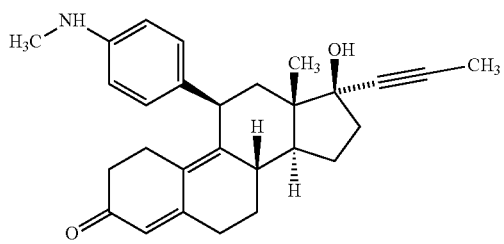

An embodiment relates to a pharmaceutical composition comprising an effective amount of mifepristone, wherein the level of N-Desmethyl mifepristone impurity is preferably not more than about 1% (w/w), more preferably not more than about 0.8% (w/w), as measured by HPLC, when stored at 25° C./60% RH for at least 3 months.

Nano-Suspension of Mifepristone

The term "nano-suspension" refers to colloidal, solid-liquid systems with a particle size of less than one micrometer. In general, nano-suspensions are stabilized by suspension-aid.

In one embodiment, the invention relates to pharmaceutical composition comprising a therapeutically effective amount of mifepristone particles and one or more pharmaceutical acceptable excipient, wherein the mifepristone particles have a $D_{90}$ equal to or less than about 1000 nm.

Surprisingly and unexpectedly, it has been found that compositions for tablets comprising up to 300 mg, mifepristone particles having a D90 (90% of the volume) less than 1000 nm lead to consistent and improved in-vivo dissolution in humans (at physiologic pH), hence, consistent and improved exposure to mifepristone and glucocorticoid receptor inhibition that will lead to consistency in therapeutic effect with improved safety profile. Accordingly, the invention provides a pharmaceutical composition comprising mifepristone particles having a D90 equal to or less than about 1000 nm as measured by a laser light scattering method, and a pharmaceutically acceptable diluent. It is preferred that the mifepristone particles in the composition have a D90 not exceeding 1000 nm. It is noted the notation DX means that X % of the volume of particles have a diameter less than a specified diameter D. Thus a D90 of 1000 nm means that 90% of the volume of particles in an mifepristone composition have a diameter less than 1000 nm.

The range of particle sizes preferred for use in the invention is D90 less than 1000 nm, more preferably D90 less than 900 nm, even more preferably D90 less than 800 nm, and most preferably D90 less than 700 nm. The particle sizes stipulated herein refer to particle sizes were determined using a laser light scattering technique.

In one embodiment, the invention relates to a stable nano-suspension comprising: (a) nano-sized mifepristone; and (b) one or more pharmaceutically acceptable excipients are selected from suspension-aid, diluents, binders, disintegrants, lubricants, glidants, surfactants, solubilizers, plasticizers, surface stabilizers, antioxidants, coloring agent, coating agent, flavors, preservatives, and combinations thereof.

In one embodiment, the invention relates to a stable nano-suspension comprising: (a) nano-sized mifepristone; and (b) at least one suspension-aid.

In one embodiment, the invention relates to a stable nano-suspension comprising: (a) nano-sized mifepristone; (b) at least one suspension-aid; (c) at least one surfactant, and (d) at least one surface stabilizer.

In other embodiment, the invention relates to a stable nano-suspension comprising: (a) nano-sized mifepristone; and (b) hydroxypropyl methylcellulose; and (c) at least one surfactant.

In other embodiment, the invention relates to a stable nano-suspension comprising: (a) nano-sized mifepristone; (b) nano-suspension-aid; and (c) sodium lauryl sulphate and (d) docusate sodium.

In other embodiment, the invention relates to a stable nano-suspension comprising: (a) nano-sized mifepristone; (b) hydroxypropyl methylcellulose; and (c) sodium lauryl sulphate and (d) docusate sodium.

In other embodiment, the invention relates to a stable nano-suspension comprising: (a) mifepristone having $D_{90}$ of less than about 1000 nm; (b) at least one suspension-aid; and (c) at least one surfactant.

In other embodiment, the invention further relates to a stable nano-suspension composition comprising: (a) mifepristone having $D_{50}$ of less than about 1000 nm; (b) hydroxypropyl methylcellulose; and (c) at least one surfactant.

In other embodiment, the invention further relates to a stable nano-suspension composition comprising: (a) mifepristone having $D_{10}$ of less than about 1000 nm; (b) hydroxypropyl methylcellulose; (c) sodium lauryl sulphate and (d) docusate sodium.

In other embodiment, the invention relates to a stable nano-suspension composition comprising: (a) nano-sized mifepristone; (b) at least one suspension-aid; and (c) at least one surfactant, wherein the nano-suspension was prepared by wet-media milling process.

In other embodiment, the invention relates to a stable nano-suspension composition comprising: (a) nano-sized mifepristone having an average particle size of less than about 1000 nm; (b) at least one suspension-aid; and (c) at least one surfactant, wherein the nano-suspension was prepared by wet-milling process.

In a further embodiment, the process for preparing nano-suspension of mifepristone comprises (a) adding at least one surfactant to the purified water in a suitable container, (b) adding mifepristone to step (a) and stirred continuously to obtain mifepristone dispersion, (c) homogenizing the above mifepristone dispersion to obtain mifepristone slurry and (d) nano-sizing mifepristone slurry in a ball-mill chamber to obtain nano-suspension containing desired particle size of mifepristone.

In a further embodiment, the process for preparing nano-suspension of mifepristone comprises (a) adding at least one suspension-aid to the purified water in a suitable container, (b) adding mifepristone to step (a) and stirred continuously to obtain mifepristone dispersion, (c) homogenizing the above mifepristone dispersion to obtain mifepristone slurry and (d) nano-sizing mifepristone slurry in a ball-mill chamber to obtain nano-suspension containing desired particle size of mifepristone.

In a further embodiment, the process for preparing nano-suspension of mifepristone comprises (a) adding at least one suspension-aid and at least one surfactant to the purified water in a suitable container, (b) adding mifepristone to step (a) and stirred continuously to obtain mifepristone dispersion, (c) homogenizing the above mifepristone dispersion to obtain mifepristone slurry and (d) nano-sizing mifepristone slurry in a ball-mill chamber to obtain nano-suspension containing desired particle size of mifepristone.

In a further embodiment, the process for preparing nano-structured mifepristone comprises a) adding at least one surfactant to the purified water in a suitable container, b) adding at least one suspension-aid to step (a) with continuous stirring, c) optionally, adding at least one additional excipient to the step (b); d) adding mifepristone to step (c) with continuous stirring to obtain mifepristone dispersion; e) homogenizing the above mifepristone dispersion to obtain mifepristone slurry; and f) nano-sizing mifepristone slurry in ball-mill to obtain nano-suspension containing desired particle size of mifepristone.

In another embodiment, the process for preparing nano-suspension mifepristone comprises a) adding specified amount of docusate sodium to the purified water in a suitable container, b) adding sodium lauryl sulphate (KOLLIPHOR® SLS Fine) to the step (a) and stirred continuously to obtain a solution, c) adding HPMC (METHOCEL® E5 LV/METHOCEL® E3 LV) to the step (b) and stirred continuously to obtain a solution, d) adding mifepristone was added to the step (c) and stirred for 5 minutes to obtain mifepristone dispersion, and e) homogenizing the above mifepristone dispersion using IKA's Ultra TURRAX® homogenizer at about 1000 RPM for 15 minutes. The above homogenized mifepristone slurry was nano-sized in a ball-mill chamber to obtain nano-suspension containing mifepristone of desired particle size.

The homogenizer is a laboratory or industrial equipment used for the homogenization of various types of materials not limited to drugs. Different models of homogenizers were available based on various physical technologies for disruption. The mortar and pestle, is used for thousands of years, is a standard tool even in modern laboratories. The more modern solutions are based on blender type instruments, bead mills, ultrasonic treatment (also sonication), rotor-stator mechanical, high pressure, and many other physical forces. For example, there are different types of homogenizers are available for the same piece of mechanical homogenizing equipment, including Cell Lysor, Disperser, High Shear Mixer, Homogenizer, Polytron, Rotor Stator Homogenizer, Sonicator or Tissue Tearor.

In an embodiment, milling or nano-micronization can also be performed to achieve desired particle sizes or distributions. Equipment that may be used for particle size reduction include, without limitation, ball mills, roller mills, hammer mills, and jet mills. Methods that may be used for particle size reduction include co-precipitation, wet suspension/dispersion milling, dry powder milling & homogenization.

In an embodiment, the ball mill comprises a vessel or vial filled with balls, or rods, constructed from a variety of materials such as ceramic, agate, silicon nitride, sintered corundum, zirconia, chrome steel, Cr-Ni steel, tungsten carbide or plastic polyamide. The material to be milled is placed inside the vessel, which is made to rotate or vibrate at a particular speed or frequency. The movement of the vessel causes the balls to cascade or move in a particular pattern, colliding with each other and with the opposing inner wall of the vessel. Size reduction of the drug particles is affected from the impact they receive from the balls as well as attritive forces arising from the movement of the balls relative to each other. The quantities of the balls and starting material determine the extent of fill of the vessel and the intensity of the milling process. Typically, the vessel is filled by the balls and starting material to 50% and 25% of the total volume of the vessel, respectively, although variations exist in the literature. In the case of a rotating vessel, rotation is usually carried out at 50-85% of the critical speed, defined as the speed at which the balls cease to cascade owing to the centrifugal force imparted by the rotating vessel. Apart from its comminution function, ball milling also serves as an intensive mixing technique capable of producing co-ground drug-excipient mixtures comprising amorphous drug forms intimately mixed with suitable hydrophilic excipients at the molecular level.

In a further embodiment, the present invention relates to a process for preparing a nano-suspension of mifepristone comprising: (i) providing an admixture of mifepristone, an aqueous dispersion medium, and milling media; and (ii) applying acoustic energy having a frequency of from about 10 hertz to 1000 hertz to said admixture, wherein preferably the acoustic energy is a standing wave supplying a linear acceleration of from about 10 G's to about 100 G's (where "G" is the force of gravity), for a period sufficient to form a nano-suspension having a particle D50 of less than about 1 micron.

In another embodiment, the particle size distribution of mifepristone nano-suspension was measured by using Mastersizer 3000 particle analyzer. The Mastersizer 3000 uses the technique of laser diffraction to measure the particle size and particle size distribution of materials. It does this by measuring the intensity of light scattered as a laser beam passes through a dispersed particulate sample. This data is then analyzed to calculate the size of the particles that created the scattering pattern.

In some embodiments described herein, the mifepristone of the invention is distinguished by particle size analysis. In some such embodiments, the mifepristone has a primary particle size of from about 1 nm to about 1000 nm, preferably from about 10 nm to about 800 nm, or more preferably from about 100 nm to about 700 nm. In other such embodiments, the mifepristone has a primary particle size distribution characterized by: (i) a D10 value of from about 10 nm to about 200 nm; (ii) a D50 value of from about 50 nm to about 500 nm; or (iii) a D90 value of from about 100 nm to about 700 nm; or a combination of (i), (ii) and (iii).

In another embodiment, the $D_{90}$ particle size of mifepristone can be in the range of 1 to 1000 nm. Preferably, the $D_{90}$ particle size of mifepristone can be between 100 and 700 nm.

In another embodiment, the nano-suspension is separated from the milling media, preferably by decanting or by centrifuging over a sieve sized appropriately to separate the milling media from the nano-suspension.

Suspension-aids adsorb on drug particle surfaces significantly during milling and reduce the extent of nano-particle aggregation. Moreover, they reduce the interfacial tension between the hydrophobic drug particles and water, thereby increasing solubility of poorly soluble drug particles.

According to the embodiments of the invention, the pharmaceutically acceptable suspension-aid is selected from one or more of hydroxypropyl methyl cellulose acetate succiate (HPMC-AS), polyvinyl pyrrolidine and vinyl acetate (PVP/VA) copolymer, hydroxypropyl methylcellulose phthalate (HPMCP), hydroxypropyl methylcellulose (HPMC), polyethylene glycol (PEG), hydroxypropyl cellulose (HPC), carboxymethyl cellulose (CMC), methyl cellulose (MC), hydroxyl ethyl cellulose (HEC) and polyvinyl pyrrolidine (PVP). The concentration of suspension-aid ranges from about 0.5% to about 10% w/w of total composition. The weight ratio of mifepristone to suspension-aid ranges from about 20:1 to about 1:20.

According to the embodiments of the invention, HPMC is available commercially, for example, from the Dow Chemical Company under the trade designation METHOCEL™, including, for example, METHOCEL™ E3LV, METHOCEL™ E5LV, METHOCEL™ E50, and METHOCEL™ K100. METHOCEL™ E5LV is a USP grade, low viscosity HPMC having 28 to 30 (29.1) % methoxyl groups and 7 to 12 (9)% hydroxypropyl group substitution. As used herein, hydroxypropyl methylcellulose E5 refers to hydroxypropyl cellulose have a viscosity of about 5 (4 to 6) mPas (cps), and hydroxypropyl methylcellulose E50 refers to hydroxypropyl cellulose have a viscosity of about 50 (40 to 60) mPas (cps). The viscosity for the hydroxypropyl cellulose is measured in a 2 weight % solution in water at 20° C. with a Ubbelohde tube viscometer.

In some embodiments, the suspension-aid is combined with a surfactant to help maintain dispersion. As is known, the nature and amount of surfactant employed will depend upon the suspension-aid employed and the nature of the surface of the particles of the active ingredient. Preferable surfactant suitable for use in nano-suspensions of the present invention include, but not limited to, sodium lauryl sulfate (SLS).

The pharmaceutical compositions of the present invention optionally may include one or more other surfactants. The other surfactants can be selected from hydrophilic surfactants or lipophilic surfactants or mixtures thereof. The surfactants can be anionic, nonionic, cationic, and zwitterionic surfactants. Surfactants according to the present invention include, but not limited to, polyoxyethylene alkylaryl ethers such as polyoxyethylene lauryl ether, polyoxyethylene cetyl ether, polyoxyethylene stearyl ether; polyethylene glycol fatty acid esters such as PEG monolaurate, PEG dilaurate, PEG distearate, PEG dioleate; polyoxyethylene sorbitan fatty acid ester such as sorbitan fatty acid mono esters such as sorbitan monolaurate, sorbitan monooleate, sorbitan sesquioleate, sorbitan trioleate, sodium lauryl sulfate, lecithin, stearylic alcohol, cetostearylic alcohol, cholesterol, polyoxyethylene ricin oil, polyoxyethylene fatty acid glycerides, Kolliphor® RH 40, polyethylene glycol 400 distearate, polyethylene glycol-20 dioleate, polyethylene glycol 4-150 mono dilaurate, and polyethylene glycol-20 glyceryl stearate; alcohol-oil transesterification products, for example, polyethylene glycol-6 corn oil; polyglycerized fatty acids, for example, polyglyceryl-6 pentaoleate; propylene glycol fatty acid esters, for example, propylene glycol monocaprylate; mono and diglycerides, for example, glyceryl ricinoleate; sterol and sterol derivatives; sorbitan fatty acid esters and its derivatives, for example, polyethylene glycol-20 sorbitan monooleate and sorbitan monolaurate; polyethylene glycol alkyl ether or phenols, for example, polyethylene glycol-20 cetyl ether and polyethylene glycol-10-100 nonyl phenol; sugar esters, for example, sucrose monopalmitate; ionic surfactants, for example, sodium caproate, sodium glycocholate, soy lecithin, sodium stearyl fumarate, propylene glycol alginate, octyl sulfosuccinate disodium, and palmitoyl carnitine; and the like and mixtures thereof. The concentration of surfactant ranges from about 0.05% to about 10% w/w of total composition. The weight ratio of mifepristone to surfactant ranges from about 50:1 to about 1:50.

Nanonization (the process of making the particles nano-sized) may be performed in the presence of a surfactant. The absorption of nano-sized particles of mifepristone into the bloodstream of a mammal may be significantly improved when the mifepristone is administered to the mammal as a formulation with a surfactant.

The present disclosure is directed to pharmaceutical compositions comprising nano-sized mifepristone. The compositions comprise nano-sized mifepristone and at least one surface stabilizer that is preferably adsorbed on or associated with the surface of the drug. The nano-sized mifepristone particles have an effective average particle size of less than about 1 micron.

The choice of a surface stabilizer for a mifepristone is non-trivial and required extensive experimentation to realize a desirable formulation. Accordingly, the present invention is directed to the surprising discovery that nano-sized mifepristone, compositions can be made.

Combinations of more than one surface stabilizer can be used in the invention. Useful surface stabilizers which can be employed in the invention include, but are not limited to, known organic and inorganic pharmaceutical excipients. Such excipients include various polymers, low molecular weight oligomers, natural products, and surfactants. Surface stabilizers include nonionic, anionic, cationic, ionic, and zwitterionic surfactants. The concentration of surface stabilizers range from about 0.05% to about 1% w/w of total composition. The weight ratio of mifepristone to suspension-aid ranges from about 20:1 to about 1:20, preferably from about 10:1 to about 1:10, more preferably from about 2:1 to about 1:2.

Representative examples of surface stabilizers useful in the invention include, but are not limited to, hydroxypropylcellulose, polyvinylpyrrolidone, dioctyl sulfosuccinate (docusate sodium), gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hypromellose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-1OG® or Surfactant 10-G® (Olin Chemicals, Stamford, Conn.); Crodestas SL40® (Croda, Inc.); and SA9OHCO, which is C18H37CH2(CON(CH3)-CH2(CHOH)4 (CH2OH)2 (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, and the like.

In further embodiment, the nano-suspension of mifepristone can be blended or sprayed over one or more intragranular excipients, as described herein, and then granulated and/or compacted with extra-granular excipients to produce a final blend for encapsulating or tableting.

The inventors of the present application have surprisingly found that a composition comprising nano-sized mifepristone, comprising at least one suspension-aid and at least one surfactant, can increase the solubility of mifepristone in gastrointestinal tract, and can ameliorate the problem of precipitation or crystallization, thereby increasing the absorption of mifepristone in vivo and enhance the bioavailability thereof.

In an aspect, the inventive composition can alter the absorption behavior of mifepristone in vivo, increasing $C_{max}$ and AUC in fasting and fed states.

Pharmaceutical Compositions Comprising Nano-Suspensions of Mifepristone

The nano-suspension may be used for preparing one of the unit dosages forms described herein (e.g., capsule or tablet). The nano-suspension can optionally be further processed before filling or tableting. Exemplary further processing includes spheronizing, pelletizing, milling, injection molding, sieving, and/or calendaring.

Nano-suspension produced by wet media milling are typically stabilized against particle agglomeration using either steric (by means of polymers or nonionic surfactants) or electrostatic (by means of ionic surfactants) stabilization mechanisms, or sometimes a combination of both mechanisms which is referred to as electro-steric stabilization. Although there is one instance of a nano-suspension product being marketed in the liquid form (MEGACE® ES), conversion of a nano-suspension into a dried powder form that can be further filled into capsules or compressed into tablets is often desirable to ensure the maximum patient compliance. The drying step can be further necessitated by the fact that there could be possible stability issues, both physical (such as Ostwald ripening and agglomeration) and chemical (such as hydrolysis) associated with nano-particles in their suspended form. Additionally, for nano-particles, there could also be a risk of crystallization upon storage if partial surface amorphization occurs during the wet milling process.

In an embodiment nano-suspension can be best transformed to oral products by various methods of solidification but not limited to lyophilization, spray drying, pelletization, electro-spraying and sprayed onto granular material. Stability profile of nano-suspension always remains a constraint due to thermodynamically active and electrostatically charged state of nano-suspension, making them more prone to Ostwald ripening and agglomeration. To minimize the aggregation problem and improve the stability, nano-suspensions may be dried to form nanocrystals, which still possess the unique properties of the nano-suspensions. Solidification techniques are best suited for the purpose of stabilization, as well as easy conversion of nano-suspension to solid form, without compromising the solubility advantages offered by technique.

Freeze-drying and spray drying are one of the most common processes used to convert a nano-suspension into a solid form. Both these processing methods result in powders that require further processing to improve the bulk density and flow properties prior to conversion into a tablet or a capsule dosage form. Granulation based approaches, which typically result in densification with improved flow properties of the powder, have also been used.

In an embodiment, the nano-suspension of mifepristone may be combined with pharmaceutically acceptable excipients to manufacture inventive pharmaceutical compositions. The one or more pharmaceutically acceptable excipients are selected from suspension-aid, diluents, binders, disintegrants, lubricants, glidants, surfactants, solubilizers, plasticizers, surface stabilizers, antioxidants, coloring agent, coating agent, flavors, preservatives, and combinations thereof.

In an embodiment, inventive pharmaceutical compositions comprising nano-sized mifepristone and pharmaceutically acceptable excipients are prepared by using, but not limited, to wet granulation, dry granulation, and direct compression.

The pharmaceutical compositions comprising nano-sized mifepristone and pharmaceutically acceptable excipients are prepared by wet granulation, which process comprises spraying nano-suspension of mifepristone over intra-granular material. The sprayed granules were dried and sieved. The sprayed and sieved intra-granular material is mixed with extra-granular material and compressed using tablet compression machine. The tablets were coated with suitable coating materials.

The process for preparation of inventive pharmaceutical composition comprises, spraying nano-sized mifepristone suspension on warmed intra-granular material (silicified microcrystalline cellulose and/or sodium starch glycolate). The sprayed granules are dried at a temperature of 50° C. to 65° C. and sieved through 30 number mesh sieves. The sieved intra-granular material is mixed with extra-granular excipients like sodium starch glycolate (PRIMOJEL®), microcrystalline cellulose (CEOLUS® KG-802), and magnesium stearate (LIGAMED® MF-2-V) and compressed using tablet compression machine. The tablets were coated with suitable coating materials.

The pharmaceutical compositions comprising nano-sized mifepristone and pharmaceutically acceptable excipients are prepared by wet granulation or dry granulation, which process comprises mixing nano-suspension of mifepristone with intra-granular excipients. The mixed granules were dried and sieved. The dried intra-granular granules were mixed with extra-granular excipients and compressed using tablet compression machine. The tablets were coated with suitable coating materials.

In an embodiment, pharmaceutical compositions comprising nano-sized mifepristone and pharmaceutically acceptable excipients are prepared using direct compression, which process comprises mixing nano-suspension of mifepristone and pharmaceutically acceptable excipients, and the resultant mixture is either compressed to tablet or filled in hard gelatin capsules.

The pharmaceutical composition of the present invention is preferably a granulate/particulate material. The granules/particles may be filled into a capsule or compressed into a tablet. The tablet may optionally be coated with an additional enteric polymer or an immediate-release film coating.

The granules of the present invention may be formulated into any suitable dosage form, including but not limited to oral suspensions, gels, tablets, capsules, immediate release formulations, delayed release formulations, controlled release formulations, extended-release formulations, pulsatile release formulations, and mixed immediate and controlled release formulations.

Other pharmaceutically acceptable excipients may include, but are not limited to, diluents, binders, disintegrating agents, surfactants, surface stabilizers, plasticizers, lubricants, glidants, chelating agents, coating agents and the like or mixtures thereof as extra-granular agents.

Suitable diluents include microcrystalline cellulose, silicified microcrystalline cellulose, calcium carbonate, calcium phosphate-dibasic, calcium phosphate-tribasic, calcium sulfate, cellulose powdered, dextrates, dextrins, dextrose excipients, fructose, kaolin, lactitol, lactose, mannitol, sorbitol, starch, starch pregelatinized, sucrose, sugar compressible, sugar confectioners and the like.

In an embodiment, diluent is included either in nano-suspension or intra-granular material or extra-granular material or both. The diluent concentration ranges from about 10% to about 60% w/w of total composition. The diluent concentration in the intra-granular material ranges from about 10% to about 60% w/w of total composition, preferably about 25% to about 35%.

Suitable binders include methyl cellulose, hydroxypropyl cellulose, hydroxypropyl methylcellulose, polyvinyl pyrrolidone, microcrystalline cellulose, gelatin, gum arabic, ethyl cellulose, polyvinyl alcohol, pullulan, pregelatinized starch, agar, tragacanth, sodium alginate, propylene glycol and the like. The concentration of binder ranges from about 1% to about 20% w/w of total composition, preferably about 10% to about 15% w/w.

Suitable disintegrating agents include croscarmellose sodium, low substituted hydroxypropyl cellulose (L-HPC), sodium starch glycollate, carboxymethyl cellulose, calcium carboxymethyl cellulose, sodium carboxymethyl cellulose, starch, crystalline cellulose, hydroxypropyl starch, pregelatinized starch, and the like and mixtures thereof. The concentration of disintegrating agent ranges from about 1% to about 10% w/w of total composition.

Suitable lubricants or glidants include colloidal silicon dioxide (AEROSIL®), stearic acid, magnesium stearate, calcium stearate, talc, hydrogenated castor oil, sucrose esters of fatty acid, microcrystalline wax, yellow beeswax, white beeswax, and the like and mixtures thereof. The concentration of lubricant or glidant ranges from about 0.5% to about 5% w/w of total composition.

Suitable colouring agent include dyes and pigments such as iron oxide red or yellow, titanium dioxide, talc. The concentration of colouring agent ranges from about 0.1% to about 1% w/w of total composition.

Suitable chelating agents include, one or more of, but not limited to ethylenediaminetetraacetic acid (EDTA), disodium EDTA and derivatives thereof, citric acid and derivatives thereof, niacinamide and derivatives thereof, and sodium desoxycholate and the like or mixtures thereof. The concentration of chelating agent ranges from about 0.1% to about 1% w/w of total composition.

Suitable antioxidants include, one or more of, but not limited to α-tocopherol, butylated hydroxytoluene (BHT), butylated hydroxyanisole (BHA), tert-butylhydroquinone (TBHQ), propyl gallate (PG) and the like or mixtures thereof. The concentration of antioxidant ranges from about 0.1% to about 1% w/w of total composition.

The pharmaceutical composition may also optionally be coated, i.e., seal coated and/or enteric coated and/or film coated. Preferably, the pharmaceutical composition may be seal coated and finally film coated or it may be seal coated and further enteric coated. Optionally, pharmaceutical compositions of the invention may be film coated. Preferably, the film coating polymer may be present in an amount from about 1 to 10% w/w.

The in vitro dissolution rate may be determined using an USP Apparatus II at 75 RPM (Rotation Per Minute), in 0.01N HCL 900 mL dissolution media at 37° C. In certain aspects, the in vitro release rate is chosen such that the in vivo peak plasma levels of mifepristone occur between about 5 minutes to about 6 hours after administration of the composition to a patient. In certain embodiments, not less than 50% of mifepristone is released after about 30 minutes. In other aspects, the in vitro dissolution rate is not less than about 50% in 60 minutes.

In certain embodiments, the inventive pharmaceutical compositions suitable for oral administration comprising nano-sized mifepristone, wherein at least 50% of the mifepristone is released after about 30 minutes as determined using USP Apparatus II at 75 RPM in 0.01N HCL 900 mL dissolution media at 37° C.

In certain embodiments, the inventive pharmaceutical compositions suitable for oral administration comprising nano-sized mifepristone, wherein at least 50% of the mifepristone is released after about 60 minutes as determined using USP Apparatus II at 75 RPM in 0.01N HCL 900 mL dissolution media at 37° C.

The in vitro dissolution rate may be determined using an USP Apparatus II at 50 RPM (Rotation Per Minute), in pH 1.8 KCl buffer 900 mL dissolution media at 37° C. In certain aspects, the in vitro release rate is chosen such that the in vivo peak plasma levels of mifepristone occur between about 5 minutes to about 6 hours after administration of the composition to a patient. In certain embodiments, not less than 50% of mifepristone is released after about 30 minutes. In other aspects, the in vitro dissolution rate is not less than about 50% in 60 minutes. In certain embodiments, not less than 70% of mifepristone is released within 45 minutes of dissolution.

In one embodiment, the invention relates to a pharmaceutical composition comprising a therapeutically effective amount of mifepristone particles, wherein the mifepristone particles have a $D_{90}$ equal to or less than about 1000 nm, and wherein, as measured using a USP Apparatus 2 at a paddle rotation speed of 50 RPM in 900 mL, of dissolution medium at 37° C., at least 70 wt % of mifepristone in the pharmaceutical composition dissolves within 45 minutes in the dissolution medium, and the dissolution medium is pH 1.8 potassium chloride buffer.

In one embodiment, the invention relates to a pharmaceutical composition comprising: (a) mifepristone; and (b) one or more pharmaceutically acceptable excipients; wherein the composition provides an in-vitro mifepristone release of not less than about 70 wt % of mifepristone, within 45 minutes of dissolution in a 900 mL pH 1.8 potassium chloride dissolution medium, measured using USP Apparatus II, at 50 RPM and 37° C.

Methods of Treatment

The compositions of the present invention may be used for the same indications as KORLYM®, including to treat high blood sugar (hyperglycemia) caused by high cortisol levels in the blood (hypercortisolism) in adults with endogenous Cushing's syndrome who have type 2 diabetes mellitus or glucose intolerance and have failed surgery or cannot have surgery.

The present invention provides methods of therapeutically treating Cushing's syndrome by administering a quantity of: a composition of the invention; or dosage form comprising a composition of the invention, administered dose ranges from about 100 mg to about 1200 mg of mifepristone per day, either in a single or divided dose. In some embodiments it is preferred to administer daily, in either a single or divided dose an amount of composition of the invention or dosage form comprising a composition of the invention which provides from about 100 mg to about 1200 mg of mifepristone per day.

The pharmaceutical composition according to the present invention improves dissolved mifepristone for absorption of mifepristone in human body and enhances bioavailability of the drug in comparison to the commercially available product (KORLYM®).

The seven or more daily doses of mifepristone can each be administered by any means suitable, as described in more detail below. In some embodiments, each of the seven or more daily doses of mifepristone are administered orally. The seven or more daily doses of mifepristone can each be administered in any suitable dose. For example, the mifepristone can be administered in an amount of at least about 100 mg. The mifepristone can also be administered in an amount of about 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190 or about 1200 mg. In some embodiments, the daily dose can be at least 240 mg. In some embodiments, the daily dose can be at least 300 mg. In some embodiments, the daily dose can be at least 600 mg. In some embodiments, the daily dose can be at least 480 mg. In some embodiments, the daily dose can be at least 720 mg. In some embodiments, the daily dose can be at least 900 mg. In some embodiments, the daily dose can be at least 960 mg. In some embodiments, the daily dose can be at least 1200 mg. Other daily doses are useful in the method of the present invention.

The daily doses can be administered for any suitable period of time that is at least 7 days in length. For example, the daily doses can be for 7, 8, 9, 10, 11, 12, 13, 14, 15, 16, 17, 18, 19, 20, 21, 22, 23, 24, 25, 26, 27, or 28 days. The mifepristone can be administered for longer periods as required by the patient being treated. In some embodiments, the patient can be treated with 28 or more daily doses over a period of 28 or more days.

The mifepristone blood levels can be tested by any means known to one of skill in the art. For example, the testing can be performed by a plasma sampling collection device suitable for detecting mifepristone serum levels.

The present invention provides a method for improving efficacy of mifepristone treatment in a patient suffering from Cushing's syndrome. The method includes treating the patient with seven or more daily doses of mifepristone over a period of seven or more days; testing the serum levels of the patient to determine whether the blood levels of mifepristone are greater than 1631 ng/mL; and adjusting the daily dose of the patient to achieve mifepristone blood levels greater than 1631 ng/mL.

The mifepristone blood levels can be at any suitable level to treat Cushing's syndrome. For example, the mifepristone blood levels can be greater than about 1400 ng/mL, 1450, 1500, 1550, 1600, 1650, 1700, 1750, 1800, 1850, 1900, 2100, 2200, 2300, 2400, 2500, 2600, 2700, 2800 or greater than about 2900 ng/mL. In some embodiments, the mifepristone blood level can be greater than 1450 ng/mL. In some embodiments, the mifepristone blood level can be greater than 1469 ng/mL. In some embodiments, the mifepristone blood level can be greater than 1600 ng/mL. In some embodiments, the mifepristone blood level can be greater than 1631 ng/mL. In some embodiments, the mifepristone blood level can be greater than 1662 ng/mL. In some embodiments, the mifepristone blood level can be greater than 1666 ng/mL. In some embodiments, the mifepristone blood level can be greater than 1700 ng/mL. In some embodiments, the mifepristone blood level can be greater than 1800 ng/mL. In some embodiments, the mifepristone blood level can be greater than 1820 ng/mL. In some embodiments, the mifepristone blood level can be greater than 2000 ng/mL. In some embodiments, the mifepristone blood level can be greater than 2022 ng/mL.

The daily dose can be adjusted to any suitable dose to maintain the mifepristone blood level above the necessary level. For example, if the mifepristone blood level is below 1631 ng/mL, the daily dose can be increased to 600 mg from 300 mg, to 900 mg from 600 mg, to 900 mg from 300 mg, to 1200 mg from 900 mg, to 1200 mg from 600 mg, or to 1200 mg from 300 mg. If after another seven daily doses, the mifepristone blood level is still not above the necessary level, the mifepristone daily can again be increased. For example, the mifepristone daily dose can be increased to 900 mg from 600 mg, to 1200 mg from 900 mg, or to 1200 mg from 600 mg. In some embodiments, the adjusting step comprises increasing the daily dose of the patient to achieve mifepristone blood levels greater than 1631 ng/mL. Additional adjustments in the daily doses can be made to maintain the mifepristone blood level above 1631 ng/mL.

The daily dose can be adjusted to any suitable dose to maintain the mifepristone blood level above the necessary level. For example, if the mifepristone blood level is below 1631 ng/mL, the daily dose can be increased to 480 mg from 240 mg, to 720 mg from 480 mg, to 720 mg from 240 mg, to 960 mg from 720 mg, to 960 mg from 480 mg, or to 960 mg from 240 mg. If after another seven daily doses, the mifepristone blood level is still not above the necessary level, the mifepristone daily can again be increased. For example, the mifepristone daily dose can be increased to 720 mg from 480 mg, to 960 mg from 720 mg, or to 960 mg from 480 mg. In some embodiments, the adjusting step comprises increasing the daily dose of the patient to achieve mifepristone blood levels greater than 1631 ng/mL. Additional adjustments in the daily doses can be made to maintain the mifepristone blood level above 1631 ng/mL.

In an embodiment, the inventive pharmaceutical composition of mifepristone is used to control hyperglycemia secondary to hypercortisolism in adult patients with endogenous Cushing's syndrome who have type 2 diabetes mellitus or glucose intolerance and have failed surgery or are not candidates for surgery.

In other embodiment, the inventive pharmaceutical composition of mifepristone is used in a regimen with misoprostol, for the medical termination of intrauterine pregnancy through 70 days gestation.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

For administration to animal or human subjects, the pharmaceutical compositions comprise an effective dosage amount of mifepristone or a pharmaceutically acceptable salt thereof. The composition may be prepared using conventional methods, for example, depending on the subject to be treated, the mode of administration, and the type of treatment desired (e.g., prevention, prophylaxis, or therapy).

The dosage levels can be dependent on the nature of the condition, drug efficacy, the condition of the patient, the judgment of the practitioner, and the frequency and mode of administration. The unit dosage forms can be administered to achieve any daily amount described herein, such as by administering one to five times daily (e.g., one, two, three, four, or five times daily).

Analysis of Samples Withdrawn During In Vitro Dissolution Study

The samples withdrawn from the dissolution study and were analyzed for assay and dissolution release using the following HPLC procedure. The materials and general conditions are listed below:

TABLE 1

Chromatographic conditions for in-vitro dissolution and Assay analysis

| | |
|---|---|
| System | HPLC system equipped with UV/PDA detector |
| Column | Xterra RP18 150 × 4.6 mm, 5 μm |
| Wavelength | 250 nm |
| Flow rate | 1.0 mL/minute |
| Injection volume | 10 μL |
| Column temperature | 40° C. ± 2° C. |
| Sample temperature | 25° C. ± 2° C. |
| Run time | 10 minutes |
| Retention time | about 4 to 7 minutes |
| Mobile Phase A | Weigh and transfer 6.8 g of sodium dihydrogen phosphate monohydrate into 1000 mL of water and mix to dissolve and observe the pH 4.50 ± 0.05. If required, adjust with ortho-phosphoric acid or 1N Sodium hydroxide solution, and filter through 0.45 μ membrane filter. |
| Mobile Phase B | Mix 800 mL of acetonitrile and 200 mL methanol degas. |
| Mode of Elution | Isocratic (Mobile Phase A: Mobile Phase B: 40:60) |

TABLE 2

Related substances identification by HPLC Chromatographic conditions

| | |
|---|---|
| System | HPLC system equipped with UV/PDA detector |
| Column | Xterra RP18 150 × 4.6 mm, 5 μm |
| Wavelength | 250 nm |
| Flow rate | 1.0 mL/minute |

TABLE 2-continued

Related substances identification
by HPLC Chromatographic conditions

| | |
|---|---|
| Injection volume | 10 μL |
| Column temperature | 40° C. ± 2° C. |
| Sample temperature | 25° C. ± 2° C. |
| Run time | 30 minutes |
| Retention time | about 13 to 14 minutes |
| Mobile Phase A | Weigh and transfer 6.8 g of sodium dihydrogen phosphate monohydrate into 1000 mL of water and mix to dissolve and observe the pH 4.50 ± 0.05. If required, adjust with ortho-phosphoric acid or 1N Sodium hydroxide solution, and filter through 0.45 μ membrane filter. |

TABLE 2-continued

Related substances identification
by HPLC Chromatographic conditions

| | |
|---|---|
| Mobile Phase B | Mix 800 mL of acetonitrile and 200 mL methanol degas. |
| Mode of Elution | Gradient |

TABLE 3

Gradient program

| Time (min) | % Mobile phase-A | % Mobile phase-B |
|---|---|---|
| 0.01 | 60 | 40 |
| 5 | 50 | 50 |
| 10 | 50 | 50 |
| 15 | 10 | 90 |
| 20 | 10 | 90 |
| 25 | 60 | 40 |
| 30 | 60 | 40 |

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

Example 1

TABLE 4

Quantitative formula for mifepristone nano-suspension (mg/unit)

| | Compositions of Mifepristone nano-suspension | | | |
|---|---|---|---|---|
| Ingredients | Composition A | Composition B | Composition C | Composition D |
| Batch size | 250 tablets | 750 tablets | 250 tablets | 250 tablets |
| Mifepristone | 300 mg | 300 mg | 300 mg | 300 mg |
| HPMC (METHOCEL® E5 LV) | 25 mg | 25 mg | 25 mg | 25 mg |
| HPMC (METHOCEL® E3 LV) | — | — | — | 8.0 mg |
| Sodium lauryl sulphate (KOLLIPHOR® SLS) | 8 mg | 8 mg | 8 mg | — |
| Docusate sodium | 1 mg | 1 mg | 1 mg | 1 mg |
| Purified water | Q.S. | Q.S. | Q.S. | Q.S. |
| Milling parameters | | | | |
| Chamber capacity | 200.00 mL | 200.00 mL | 200.00 mL | 200.00 mL |
| Zirconium beads size | 0.3 mm | 0.3 mm | 0.2 mm | 0.3 mm |
| Agitator speed | 1750 | 2500 | 2500 | 2500 |

Manufacturing Procedure of Composition A, B, C and D

Compositions A, B, C and D were manufactured according to the following procedure:
a) Specified amount of purified water was taken in a suitable container and added specified quantity of docusate sodium under continuous stirring to obtain a solution.
b) Sodium Lauryl Sulphate (KOLLIPHOR® SLS Fine) was added to the step (a) solution and stirred continuously to obtain a solution.
c) HPMC (METHOCEL® E5 LV/METHOCEL® E3 LV) was added to the step (b) solution and stirred continuously to obtain a solution.
d) Mifepristone was added to the step (c) solution and stirred for 5 minutes to obtain mifepristone dispersion.
e) Homogenized the above mifepristone dispersion using IKA's Ultra TURRAX® homogenizer at 1000 RPM for 15 minutes.
f) The above homogenized mifepristone slurry was nano-sized in ball-mill chamber to obtain a nano-suspension containing the desired particle size of mifepristone. The particle size distribution was measured using a Mastersizer 3000 particle analyser.

Particle Size Distribution of Mifepristone in Composition A

Homogenized mifepristone slurry of Composition A was ball-milled at a speed of 1730 RPM at 30° C. for 80 minutes and further milled at 10° C. for 70 minutes, using the conditions set forth in Tables 5 and 6.

TABLE 5

At the Input temperature of 30° C.:

| | Running Time (minutes) | | | | | |
|---|---|---|---|---|---|---|
| | Initial | 15 | 30 | 45 | 60 | 80 |
| Agitator Speed (RPM) | 1750 | 1730 | 1730 | 1730 | 1730 | 1730 |
| Temperature In (° C.) | 30 | 30 | 30 | 30 | 30 | 30 |
| Temperature Out (° C.) | 32 | 36 | 36 | 36 | 36 | 36 |
| Particle size distribution (in microns) | | | | | | |
| D10 | 0.564 | 0.39 | 0.344 | 0.322 | 0.3 | 0.287 |
| D50 | 1.6 | 0.63 | 0.5 | 0.451 | 0.424 | 0.404 |
| D90 | 3.67 | 1.88 | 0.825 | 0.64 | 0.592 | 0.561 |

TABLE 6

At the Input temperature of 10° C.:

| | Running Time (minutes) | | | |
|---|---|---|---|---|
| | Initial | 20 | 40 | 70 |
| Agitator Speed (RPM) | — | 1750 | 1750 | 1750 |
| Temperature In (° C.) | — | 10 | 10 | 10 |
| Temperature Out (° C.) | — | 22 | 22 | 22 |
| Particle size distribution (in microns) | | | | |
| D10 | 0.284 | 0.268 | 0.261 | 0.250 |
| D50 | 0.404 | 0.38 | 0.37 | 0.357 |
| D90 | 0.57 | 0.522 | 0.511 | 0.495 |

Particle Size Distribution of Mifepristone in Composition B

Homogenized mifepristone slurry of Composition B was ball-milled at speed of 2500 RPM at 20° C. for 140 minutes (see Table 7). The Composition B was stored for a period of 15 days. No significant change in particle size distribution was observed during the 15 days storage period.

TABLE 7

| | Running Time (minutes) | | | | | | | |
|---|---|---|---|---|---|---|---|---|
| | Initial | 20 | 40 | 60 | 80 | 100 | 120 | 140 |
| Agitator speed (RPM) | — | 2500 | 2500 | 2500 | 2500 | 2500 | 2500 | 2500 |
| Temperature In (° C.) | — | 20 | 20 | 20 | 20 | 20 | 20 | 20 |
| Temperature Out (° C.) | — | 25 | 25 | 25 | 25 | 25 | 25 | 25 |
| Particle size distribution (in microns) | | | | | | | | |
| D10 | 0.578 | 0.435 | 0.376 | 0.347 | 0.322 | 0.304 | 0.287 | 0.284 |
| D50 | 1.58 | 0.809 | 0.577 | 0.508 | 0.454 | 0.429 | 0.405 | 0.397 |
| D90 | 4.07 | 2.74 | 1.72 | 0.949 | 0.648 | 0.601 | 0.569 | 0.549 |

Particle Size Distribution of Mifepristone in Composition C

Homogenized mifepristone slurry of Composition C was ball-milled at speed of 2500 RPM at 20° C. for 100 minutes with 0.2 mm zirconium beads (see Table 8). Change in zirconium beads size from 0.3 mm to 0.2 mm in milling procedure does not have any significant effect on the particle size distribution of the final nano-suspension.

TABLE 8

| | Running Time (minutes) | | | | | |
|---|---|---|---|---|---|---|
| | Initial | 20 | 40 | 60 | 80 | 100 |
| Agitator Speed (RPM) | — | 2500 | 2500 | 2500 | 2500 | 2500 |
| Temperature In (° C.) | — | 20 | 20 | 20 | 20 | 20 |
| Temperature Out (° C.) | — | 24 | 26 | 26 | 26 | 26 |
| Particle size distribution (in microns) | | | | | | |
| D10 | 0.61 | 0.397 | 0.341 | 0.311 | 0.293 | 0.276 |
| D50 | 1.8 | 0.667 | 0.504 | 0.439 | 0.415 | 0.391 |
| D90 | 4.56 | 2.63 | 1.31 | 0.627 | 0.582 | 0.553 |

Particle Size Distribution of Mifepristone in Composition D

Homogenized mifepristone slurry of Composition D was ball-milled at speed of 1754 RPM at 20° C. for 15 minutes and further at a speed of 2500 RPM at 20° C. for an additional 60 minutes (see Table 9). Change in a viscosity grade of HPMC from METHOCEL® E5 LV to METHOCEL® E3 LV was found to have no effect on the particle size distribution of the final nano-suspension.

TABLE 9

| | Running Time (minutes) | | | | | |
|---|---|---|---|---|---|---|
| | Initial | 15 | 30 | 45 | 60 | 75 |
| Agitator Speed (RPM) | — | 1754 | 2500 | 2500 | 2500 | 2500 |
| Temperature In (° C.) | — | 20 | 20 | 20 | 20 | 20 |
| Temperature Out (° C.) | — | 24 | 26 | 26 | 26 | 26 |
| Particle size distribution (in microns) | | | | | | |
| D10 | 0.548 | 0.392 | 0.326 | 0.311 | 0.295 | 0.281 |
| D50 | 1.5 | 0.622 | 0.463 | 0.439 | 0.419 | 0.397 |
| D90 | 3.92 | 1.9 | 0.668 | 0.627 | 0.588 | 0.559 |

Example 2

TABLE 10

Quantitative formula for mifepristone nano-suspension (mg/unit).

| | Compositions of Mifepristone nano-suspension | |
|---|---|---|
| Ingredients | Composition E | Composition F |
| Batch size | 250 tablets | 250 tablets |
| Mifepristone | 300 mg | 300 mg |
| HPMC (METHOCEL® E5 LV) | 25 mg | 25 mg |
| Sodium Lauryl Sulphate (KOLLIPHOR® SLS) | 10 mg | — |
| Poloxamer 188 | 4 mg | — |
| Polysorbate 80 (TWEEN® 80) | — | 4 mg |
| Purified Water | Q.S. | Q.S. |
| Milling parameters | | |
| Chamber Capacity | 200.00 mL | 200.00 mL |
| Zirconium beads size | 0.3 mm | 0.3 mm |
| Agitator Speed | 1750 | 2500 |

Manufacturing Procedure of Composition E

Composition E was manufactured according to the following procedure:
a) Required amount of purified water was taken in a suitable container and specified quantity of Poloxamer 188 was added and stirred continuously to obtain a solution.
b) Sodium lauryl sulphate (KOLLIPHOR® SLS Fine) was added to the step (a) solution and stirred continuously to obtain a solution.
c) Hydroxypropyl methyl cellulose (METHOCEL® E5 LV/METHOCEL® E3 LV) was added to the step (b) solution under stirring and stirred continuously to obtain a solution.
d) Mifepristone was added to the step (c) solution and stirred for 5 minutes to obtain Mifepristone dispersion.
e) Mifepristone dispersion was homogenised using IKA's Ultra Turrax homogenizer at 1000 RPM for 15 minutes.
f) The above homogenized mifepristone slurry was nano-sized in ball-mill chamber to obtain nano-suspension containing desired particle size of mifepristone. The particle size distribution was measured by using Mastersizer 3000 particle analyser.

Manufacturing Procedure of Composition F

Composition F was manufactured according to the following procedure:
a) Specified amount of purified water was taken in a suitable container and specified quantity of TWEEN® 80 was added and stirred continuously to obtain a solution.
b) Hydroxypropyl methyl cellulose (METHOCEL® E5 LV) was added to the step (a) solution and stirred continuously to obtain a solution.
c) Mifepristone was added to the step (b) solution and stirred for 5 minutes to obtain mifepristone dispersion.
d) Mifepristone dispersion was homogenized using IKA's Ultra TURRAX® homogenizer at 1000 RPM for 15 minutes.

e) The above homogenized mifepristone slurry was nano-sized in ball-mill chamber to obtain nano-suspension containing desired particle size of mifepristone. The particle size distribution was measured by using Mastersizer 3000 particle analyser.

Particle Size Distribution of Mifepristone in Composition E

Homogenized mifepristone slurry of Composition E was ball-milled at speed of 1759 RPM at 8.5° C. for 35 minutes. It was observed that during the milling process Poloxamer 188 increases the particles agglomeration and the process was discontinued.

TABLE 11

|  | Running Time (minutes) | | | |
| --- | --- | --- | --- | --- |
|  | Initial | 5 | 15 | 35 |
| Agitator Speed (RPM) | — | 1759 | 1759 | 1759 |
| Temperature In (° C.) | — | 8.5 | 8.5 | 8.5 |
| Temperature Out (° C.) | — | 26 | 26 | 26 |
| Particle size distribution | | | | |
| D10 (in microns) | 0.578 | 0.998 | 0.833 | 1.76 |
| D50 (in microns) | 1.54 | 25.3 | 28.5 | 24 |
| D90 (in microns) | 3.59 | 51.7 | 217 | 47.5 |

Particle Size Distribution of Mifepristone in Composition F

TABLE 12

Homogenized mifepristone slurry of Composition F was ball-milled at speed of 2500 RPM at 20° C. for 100 minutes.

|  | Running Time (minutes) | | | | | |
| --- | --- | --- | --- | --- | --- | --- |
|  | Initial | 20 | 40 | 60 | 80 | 100 |
| Agitator Speed (RPM) | — | 2500 | 2500 | 2500 | 2500 | 2500 |
| Temperature In (° C.) | — | 20 | 20 | 20 | 20 | 20 |
| Temperature Out (° C.) | — | 25 | 25 | 25 | 25 | 25 |
| Particle size distribution (in microns) | | | | | | |
| D10 | 0.638 | 0.382 | 0.333 | 0.314 | 0.298 | 0.28 |
| D50 | 1.76 | 0.599 | 0.49 | 0.444 | 0.423 | 0.398 |
| D90 | 4.48 | 1.97 | 1.09 | 0.639 | 0.596 | 0.563 |

TABLE 13

The mifepristone nano-suspension was subjected to stability of 2 days.
Particle size distribution (in microns)

| Particle Size Distribution (in microns) | Initial (before milling) | Initial (after milling for 100 minutes) | Day 2 |
| --- | --- | --- | --- |
| D10 | 0.638 | 0.28 | 0.382 |
| D50 | 1.76 | 0.398 | 0.599 |
| D90 | 4.48 | 0.563 | 1.97 |

It was observed that particle size increased within 2 days and suspension was found to be unstable.

Example 3

TABLE 14

Composition of mifepristone tablet 240 mg
Composition G

| Ingredients | mg/unit |
| --- | --- |
| Mifepristone nano-suspension | |
| Mifepristone | 240.00 |
| HPMC (METHOCEL ® E5 LV) | 20.00 |
| Sodium lauryl sulphate (KOLLIPHOR ® SLS) | 6.40 |
| Docusate sodium | 0.80 |
| Purified water | Q.S. |
| Intra-granular material | |
| Silicified microcrystalline cellulose (PROSOLV ® SMCC 90) | 280.40 |
| Sodium starch glycolate (PRIMOJEL ®) | 27.20 |
| Extra-granular material | |
| Microcrystalline cellulose (CEOLUS ® KG-802) | 121.40 |
| Sodium starch glycolate (PRIMOJEL ®) | 20.40 |
| Magnesium Stearate (LIGAMED ® MF-2-V) | 3.40 |
| Core tablet weight (mg) | 720.00 |
| Film-coating blend | |
| OPADRY ® II Complete Film Coating System 85F18422 white | 21.60 |
| Purified Water | Q.S. |
| Coated Tablet Weight (mg) | 741.60 |

Manufacturing Procedure of Composition G

Composition G was manufactured according to the following procedure:

a) Specified amount of purified water was taken in a suitable container and specified quantity of docusate sodium was added and stirred continuously to obtain a solution.

b) Sodium lauryl sulphate was added to the step (a) solution and stirred continuously to obtain a solution.

c) Hydroxypropyl methyl cellulose was added to the step (b) solution and stirred continuously to obtain a solution.

d) Mifepristone was added to the step (c) solution and stirred for 5 minutes to obtain Mifepristone dispersion.

e) Mifepristone dispersion was homogenized using IKA's Ultra TURRAX® homogenizer at 1000 RPM for 15 minutes.

f) The above homogenized mifepristone slurry was nano-sized in ball-mill chamber to obtain nano-suspension containing desired particle size of mifepristone. The particle size distribution was measured by using Mastersizer 3000 particle analyser.
g) Specified quantities of the silicified microcrystalline cellulose and sodium starch glycolate were dispensed in a bowl and warmed to reach 28° C. to 30° C. temperature.
h) The nano-sized mifepristone suspension according to step (f) was sprayed onto the warmed intra-granular material according to step (g). The sprayed granules were dried at a temperature of 50° C. to 65° C. and sieved through 30 number mesh sieve.
i) Dispensed the specified quantities of milled granules of step (h), sodium starch glycolate, microcrystalline cellulose, and magnesium stearate and compressed using tablet compression machine. The tablets according to step (i) were coated with suitable coating materials.

Example 4

TABLE 15

Composition of mifepristone tablet 240 mg
Composition H

| Ingredients | mg/unit |
|---|---|
| Mifepristone nano-suspention | |
| Mifepristone | 240.00 |
| HPMC | 20.00 |
| Sodium lauryl sulphate | 6.40 |
| Docusate sodium | 0.80 |
| Purified water | Q.S. |
| Intra-granular material | |
| Silicified microcrystalline cellulose | 280.40 |
| Sodium starch glycolate | 27.20 |
| Extra-granular material | |
| Microcrystalline cellulose | 119.6 |
| Sodium starch glycolate | 20.40 |
| Colloidal silicon dioxide | 1.8 |
| Magnesium Stearate | 3.40 |
| Core tablet weight (mg) | 720.00 |
| OPADRY ® II Complete Film Coating System 85F18422 white | 21.60 |
| Purified Water | Q.S. |
| Coated Tablet Weight (mg) | 741.60 |

Manufacturing Procedure of Composition H
Composition H was manufactured according to the following procedure:
a) Specified amount of purified water was taken in a suitable container and specified quantity of docusate sodium was added and stirred continuously to obtain a solution.
b) Sodium lauryl sulphate was added to the step (a) solution and stirred continuously to obtain a solution.
c) Hydroxypropyl methyl cellulose was added to the step (b) solution and stirred continuously to obtain a solution.
d) Mifepristone was added to the step (c) solution and stirred for 5 minutes to obtain Mifepristone dispersion.
e) Mifepristone dispersion was homogenized using IKA's Ultra TURRAX® homogenizer at 1000 RPM for 15 minutes.
f) The above homogenized mifepristone slurry was nano-sized in ball-mill chamber to obtain nano-suspension containing desired particle size of mifepristone. The particle size distribution was measured by using Mastersizer 3000 particle analyser.
g) Specified quantities of the silicified microcrystalline cellulose and sodium starch glycolate were dispensed in a bowl and warmed to reach 28° C. to 30° C. temperature.
h) The nano-sized mifepristone suspension according to step (f) was sprayed onto the warmed intra-granular material according to step (g). The sprayed granules were dried at a temperature of 50° C. to 65° C. and sieved through 30 number mesh sieve.
i) Specified quantities of milled granules of step (h), sodium starch glycolate, microcrystalline cellulose, colloidal silicon dioxide and magnesium stearate were blended and compressed using tablet compression machine. The tablets according to step (i) were coated with suitable coating materials.

Example 5

Particle Size Distribution of Mifepristone Nano-suspensions Used in Composition G and H

TABLE 16

Process parameters of nano-milling for preparation of mifepristone nano-suspensions used in composition G and H:

| Parameters | Nano-suspension used in composition G | Nano-suspension used in composition H |
|---|---|---|
| Mifepristone slurry initial solid content | 20% | 20% |
| After rinsing of container bottle and mill | 15% | 15.8% |
| Due to additional 0.1 mm beads rinsing | NA | 14.1% |
| Size of beads used | 0.3 mm | 0.3 mm and 0.1 mm |
| Screen | 0.13 mm | 0.13 mm and 0.03 mm |
| Occupancy | 65% | 65% |
| Nano milling time | 90 minutes with 0.3 mm beads | 60 minutes with 0.3 mm beads and 80 minutes with 0.1 mm beads |
| Particle Size Distribution (PSD) of mifepristone (in microns) | | |
| D10 | 0.090 | 0.0602 |
| D50 | 0.186 | 0.122 |
| D90 | 0.369 | 0.233 |

TABLE 17

Effect of storage time on particle size distribution of mifepristone in composition G
Particle Size Distribution (PSD) (in microns)

| PSD | Initial | Day 1 | Day 3 | Day 7 | Day 15 |
|---|---|---|---|---|---|
| D10 | 0.284 | 0.288 | 0.270 | 0.267 | 0.277 |
| D50 | 0.397 | 0.404 | 0.396 | 0.394 | 0.404 |
| D90 | 0.549 | 0.561 | 0.583 | 0.584 | 0.597 |

Example 6

A study was conducted to test the pharmacokinetics and bioavailability of Composition G and H in healthy adult, human volunteers, under fed state.
This study is open label, balanced, randomized, single-dose, three-treatment, three-sequence, three-period, crossover, oral bioavailability study of Mifepristone tablet 240 mg (Composition G and H (Test products=T); Dose: 4 tablets×240 mg=960 mg) and KORLYM® (Mifepristone tablets 300 mg (Reference product=R); Dose: 4 tablets×300 mg=1200 mg) in 11 healthy, adult, male and postmenopausal female human subjects under fed condition (n=11).

TABLE 18

| Pharmaco-kinetic Parameters | Composition G Dose: 960 mg (Fed) = T Least Square Geometric Mean | KORLYM® Dose: 1200 mg (Fed) = R Least Square Geometric Mean | T/R Ratio | 90% Confidence interval (CI) (Lower-Upper) |
|---|---|---|---|---|
| Analyte: Mifepristone | | | | |
| $C_{max}$ (ng/mL) | 4060.8 | 4197.7649 | 96.74 | 85.17-109.9 |
| $AUC_{0-72\,h}$ (ng · hr/mL) | 103748.3 | 108957.73 | 95.22 | 88.63-102.3 |
| Analyte: N-mono-demethylated RU42633 | | | | |
| $C_{max}$ (ng/mL) | 2530.4682 | 2727.18 | 92.79 | 85.89-100.24 |
| $AUC_{0-72\,h}$ (ng · hr/mL) | 126139.23 | 128855 | 97.89 | 90.67-105.69 |
| Analyte: Hydroxylated RU42698 | | | | |
| $C_{max}$ (ng/mL) | 605.5 | 665.4428 | 90.99 | 83.35-99.33 |
| $AUC_{0-72\,h}$ (ng · hr/mL) | 31392.1 | 32669.123 | 96.09 | 89.39-103.3 |

TABLE 19

| Pharmaco-kinetic Parameters | Composition H Dose: 960 mg (Fed) = T Least Square Geometric Mean | KORLYM® Dose: 1200 mg (Fed) = R Least Square Geometric Mean | T/R Ratio | 90% Confidence interval (CI) (Lower-Upper) |
|---|---|---|---|---|
| Analyte: Mifepristone | | | | |
| $C_{max}$ (ng/mL) | 4615.0 | 4197.7649 | 109.94 | 99.38-121.6 |
| $AUC_{0-72\,h}$ (ng · hr/mL) | 117713.9 | 108957.73 | 108.04 | 93.6-124.7 |

TABLE 19-continued

| Pharmaco-kinetic Parameters | Composition H Dose: 960 mg (Fed) = T Least Square Geometric Mean | KORLYM® Dose: 1200 mg (Fed) = R Least Square Geometric Mean | T/R Ratio | 90% Confidence interval (CI) (Lower-Upper) |
|---|---|---|---|---|
| Analyte: N-mono-demethylated RU42633 | | | | |
| $C_{max}$ (ng/mL) | 2809.9 | 2727.1793 | 103.03 | 93.22-113.9 |
| $AUC_{0-72\,h}$ (ng · hr/mL) | 139504.4 | 128854.68 | 108.26 | 93.63-125.2 |
| Analyte: Hydroxylated RU42698 | | | | |
| $C_{max}$ (ng/mL) | 664.80 | 665.44 | 99.90 | 86.71-115.11 |
| $AUC_{0-72\,h}$ (ng · hr/mL) | 34963.44 | 34963.44 | 107.02 | 93.65-122.30 |

Example 7

Dissolution Profiles of Composition G and H

TABLE 20

| Dissolution conditions: | |
|---|---|
| Apparatus | USP Type-2 (Paddle) |
| Dissolution Media | pH 1.8 potassium chloride buffer |
| Media Volume | 900 mL |
| Temperature | 37.0° C. ± 0.5° C. |
| Agitation speed | 50 RPM |
| Sampling Timepoint | 5, 10, 15, 30, 45, and 60 minutes |
| Sample Volume | 10 mL |
| Replacement Volume | 10 mL |
| Filters | 10 μ full flow filter |

TABLE 21

Assay, drug release and related substance profile:

| | KORLYM® 300 mg tablet | Composition G | | | Composition H | | |
|---|---|---|---|---|---|---|---|
| | Storage condition; duration | | | | | | |
| Time Points (minutes) | 25° C./ 60% RH | Initial | 25° C./ 60% RH; 6 M* | 40° C./ 75% RH; 6 M | Initial | 25° C./ 60% RH; 3 M* | 40° C./ 75% RH; 3 M |
| 5 | 36 | 90 | 88 | 86 | 96 | 90 | 90 |
| 10 | 77 | 91 | 89 | 88 | 97 | 91 | 91 |
| 15 | 88 | 92 | 90 | 88 | 97 | 92 | 92 |
| 30 | 94 | 92 | 91 | 89 | 98 | 93 | 93 |
| 45 | 95 | 92 | 91 | 90 | 99 | 94 | 93 |
| 60 | 96 | 93 | 92 | 90 | 99 | 94 | 94 |
| Assay (%) of Mifepristone | | | | | | | |
| % | NA | 100 | 99.8 | 100.7 | 104.1 | 101.8 | 102.6 |
| Water content measured by Karl Fisher (KF) | | | | | | | |
| % | NA | 4.1 | 3.3 | 3.3 | 2.4 | 3.7 | 3.7 |

TABLE 21-continued

Assay, drug release and related substance profile:

| | KORLYM® 300 mg tablet | Composition G | | | Composition H | | |
|---|---|---|---|---|---|---|---|
| | | Storage condition; duration | | | | | |
| Time Points (minutes) | 25° C./ 60% RH | Initial | 25° C./ 60% RH; 6 M* | 40° C./ 75% RH; 6 M | Initial | 25° C./ 60% RH; 3 M* | 40° C./ 75% RH; 3 M |
| | | | Related substance (%) | | | | |
| RS-A* | NA | 0.39 | 0.49 | 0.52 | 0.48 | 0.48 | 0.51 |
| Any single impurity | NA | 0.05 | 0.04 | 0.06 | 0.04 | 0.04 | 0.04 |
| Total impurities | NA | 0.65 | 0.70 | 0.79 | 0.80 | 0.77 | 0.80 |

*6 M = 6 months; 3 M = 3 months; RS-A = N-Demethyl mifepristone impurity; NA = Not Analyzed or Not Applicable.

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

What is claimed:

1. An oral pharmaceutical composition comprising:
   (a) a therapeutically effective dose of mifepristone having an average D90 particle size less than 1000 nm;
   (b) a surface stabilizer; and
   (c) optionally, at least one pharmaceutically acceptable excipient;
   wherein the oral pharmaceutical composition is an immediate-release pharmaceutical composition;
   wherein the oral pharmaceutical composition is a tablet or a capsule;
   wherein the oral pharmaceutical composition provides an in-vitro release of not less than about 70 wt % of the mifepristone, within 45 minutes of dissolution in a 900 mL pH 1.8 potassium chloride dissolution medium, measured using USP Apparatus II, at 50 RPM and 37° C.; and
   wherein the therapeutically effective dose of mifepristone in the oral pharmaceutical composition is reduced by at least 10% compared to therapeutically effective dose of mifepristone in a reference composition, when administered to a human subject.

2. The oral pharmaceutical composition according to claim 1, wherein a therapeutically effective dose of mifepristone administered in the pharmaceutical composition is 250 mg.

3. The oral pharmaceutical composition according to claim 1, wherein a therapeutically effective dose of mifepristone administered in the reference composition is 300 mg.

4. The oral pharmaceutical composition according to claim 1, wherein the surface stabilizer is a non-ionic surfactant, a cationic surfactant, an anionic surfactant, or a zwitterionic surfactant.

5. An oral pharmaceutical composition of claim 1, prepared by:
   (a) mixing mifepristone and a surface stabilizer with purified water, and milling to obtain a nano-suspension containing mifepristone with an average D90 particle size less than 1000 nm;
   (b) spraying the nano-suspension from (a) onto an intra-granular material and drying to obtain granules;
   (c) mixing the granules from (b) with an extra-granular material to obtain a blend; and
   (d) compressing the blend from (c) into a tablet or filling it into a capsule;
   (e) optionally, coating the tablet,
   wherein the oral pharmaceutical composition is an immediate-release pharmaceutical composition;
   wherein the oral pharmaceutical composition provides an in-vitro release of not less than about 70 wt % of the mifepristone, within 45 minutes of dissolution in a 900 mL pH 1.8 potassium chloride dissolution medium, measured using USP Apparatus II, at 50 RPM and 37° C.

6. The pharmaceutical composition according to claim 5, wherein the intra-granular material comprises at least one pharmaceutically acceptable excipient.

7. The pharmaceutical composition according to claim 5, wherein the extra-granular material comprises at least one pharmaceutically acceptable excipient.

8. The pharmaceutical composition according to claim 6, wherein the pharmaceutically acceptable excipient is selected from diluents, binders, disintegrants, lubricants, glidants, surfactants, plasticizers, solubilizers, antioxidants, or mixtures thereof.

9. The pharmaceutical composition according to claim 7, wherein the pharmaceutically acceptable excipient is selected from diluents, binders, disintegrants, lubricants, glidants, surfactants, plasticizers, solubilizers, antioxidants, or mixtures thereof.

10. The pharmaceutical composition according to claim 5, wherein the intra-granular material is selected from silicified microcrystalline cellulose, sodium starch glycolate, or mixtures thereof.

11. The pharmaceutical composition according to claim 5, wherein the extra-granular material is selected from microcrystalline cellulose, sodium starch glycolate, colloidal silicon dioxide, magnesium stearate, or mixtures thereof.

12. An oral pharmaceutical composition according to claim 5, wherein the surface stabilizer is a non-ionic surfactant, a cationic surfactant, an anionic surfactant, or a zwitterionic surfactant.

* * * * *